US011472872B2

(12) United States Patent
Furrer

(10) Patent No.: US 11,472,872 B2
(45) Date of Patent: Oct. 18, 2022

(54) ANTIBODY VARIANTS

(71) Applicant: Tillotts Pharma AG, Rheinfelden (CH)

(72) Inventor: Esther Maria Furrer, Rheinfelden (CH)

(73) Assignee: Tillotts Pharma AG, Rheinfelden (CH)

( * ) Notice: Subject to any disclaimer, the term of this patent is extended or adjusted under 35 U.S.C. 154(b) by 0 days.

(21) Appl. No.: 16/648,147

(22) PCT Filed: Sep. 11, 2018

(86) PCT No.: PCT/EP2018/074525
§ 371 (c)(1),
(2) Date: Mar. 17, 2020

(87) PCT Pub. No.: WO2019/057567
PCT Pub. Date: Mar. 28, 2019

(65) Prior Publication Data

US 2020/0277367 A1 Sep. 3, 2020

(30) Foreign Application Priority Data

Sep. 19, 2017 (EP) .................................... 17191987

(51) Int. Cl.
*C07K 16/24* (2006.01)
*A61K 39/395* (2006.01)
*C07K 16/28* (2006.01)
*A61K 9/00* (2006.01)
*A61K 39/00* (2006.01)

(52) U.S. Cl.
CPC .......... *C07K 16/241* (2013.01); *A61K 9/0014* (2013.01); *A61K 9/0053* (2013.01); *A61K 39/395* (2013.01); *A61K 39/3955* (2013.01); *A61K 39/39533* (2013.01); *A61K 2039/505* (2013.01); *C07K 16/283* (2013.01); *C07K 2317/31* (2013.01); *C07K 2317/52* (2013.01); *C07K 2317/76* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS 7,645,450 B2 1/2010 Yoo
2006/0040325 A1* 2/2006 Wu .......................... A61P 35/00
435/7.1

FOREIGN PATENT DOCUMENTS

WO WO 2017/158426 A1 9/2017

OTHER PUBLICATIONS

Paolo Biancheri et al., "Proteolytic Cleavage and Loss of Function of Biologic Agents that Neutralize Tumor Necrosis Factor in the Mucosa of Patients with Inflammatory Bowel Disease", *Gastroenterology*, vol. 149, No. 6, pp. 1564-1574 (Jul. 11, 2015).
Michelle Kinder et al., "Engineered Protease-resistant Antibodies with Selectable Cell-killing Functions", *Journal of Biological Chemistry*, vol. 288, No. 43, pp. 30843-30854 (Oct. 25, 2013).
Arvind Rajpal et al., "Introduction: Antibody Structure and Function", *Therapeutic Fc-Fusion Proteins*, First Edition, Ed. Steven Chamow et al., Wiley-VCH Verlag GmbH & Co. KGaA, Weinhein, Germany, pp. 1-44 (Feb. 19, 2014).
Rong Deng et al., *Drug Metabolism and Disposition*, vol. 38, No. 4, pp. 600-605 (Apr. 1, 2010).
Yik Andy Yeung et al., *Journal of Immunology*, vol. 182, No. 12, pp. 7663-7671 (Jun. 1, 2009).
Timothy Kuo et al., MABS, vol. 3, No. 5, pp. 422-430 (Sep. 1, 2011).
Takuo Suzuki et al., *Journal of Immunology*, vol. 184, No. 4, pp. 1968-1976 (Feb. 12, 2010).
Yasmina Noubia Abdiche et al., MABS, vol. 7, No. 2, pp. 331-343 (Mar. 4, 2015).
Sally E. Ward et al., *Molecular Immunology*, vol. 67, No. 2, pp. 131-141 (Mar. 9, 2015).
Natsume et al., *Drug Design, Development and Therapy*, vol. 3, pp. 7-16 (2009).
Jaramillo et al., MABS, vol. 9, No. 5, pp. 781-791 (May 25, 2017).
Steidl et al., *Mol. Immunol.*, vol. 46, pp. 135-144 (2008).
Wang et al., Drug Metabolism and Disposition, vol. 39, No. 9, pp. 1469-1477 (Sep. 2011).
Shields et al., JBC, vol. 276, No. 9, pp. 6591-6604 (Mar. 2001).
Lloyd et al., Protein Eng. Des. Sel. (2009), 22(3): 159-68.
Janeway et al., *Immunobiology*, 3rd edition, Garland Publishing, Inc. (1997), pp. 3:1-3:21.
Rudikoff et al., *PNAS USA* (1982), 79(6); 1979-83.
Edwards et al., *J. Mol. Biol.*, (2003), 334(1); 103-18.
Lescar et al., J. Biol. Chem. (1995), 270(30): 18067-18076.
Stryer et al., *Biochemistry*, 4th edition, W.H. Freeman and Company (1995), pp. 18-23.

* cited by examiner

*Primary Examiner* — Elizabeth C. Kemmerer
(74) *Attorney, Agent, or Firm* — Smith Patent, LLC; Chalin A. Smith

(57) ABSTRACT

The present invention relates to antibodies which bind to TNFα and comprise a modified Fc region. The antibodies of the invention have improved resistance against proteolytic degradation and good effector functions and/or pharmacokinetic properties.

13 Claims, 6 Drawing Sheets

Specification includes a Sequence Listing.

SEQUENCE LISTING

<160> NUMBER OF SEQ ID NOS: 30

<210> SEQ ID NO 1
<211> LENGTH: 221
<212> TYPE: PRT
<213> ORGANISM: Artificial Sequence
<220> FEATURE:
<223> OTHER INFORMATION: Light chain of Ab-wt, the parent antibody of the modified antibodies used in the examples (clone 16-22-H05)

<400> SEQUENCE: 1

Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Ser Ile Phe Ser Gly
            20                  25                  30

Leu Ala Trp Tyr Gln Gln Lys Pro Gly Lys Ala Pro Lys Leu Leu Ile
        35                  40                  45

Tyr Gly Ala Ser Lys Leu Ala Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Ala Asp Phe Ala Thr Tyr Tyr Cys Gln Ser Tyr Tyr Tyr Ser Ser Ser
                85                  90                  95

Ser Ser Asp Gly Ser Tyr Ala Phe Gly Gly Gly Thr Lys Leu Thr Val
            100                 105                 110

Leu Gly Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220

<210> SEQ ID NO 2
<211> LENGTH: 452
<212> TYPE: PRT
<213> ORGANISM: Artificial Sequence
<220> FEATURE:
<223> OTHER INFORMATION: Heavy chain of Ab-wt, the parent antibody of the modified antibodies used in the examples (clone 16-22-H05)

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Asn Asn Tyr
            20                  25                  30

Gly Ile Gly Trp Val Arg Gln Ala Pro Gly Lys Gly Leu Glu Trp Ile
        35                  40                  45

Thr Tyr Ile Tyr Pro Gly Phe Ala Ile Thr Asn Phe Ala Asn Ser Val
    50                  55                  60

Lys Gly Arg Phe Thr Ile Ser Ser Asp Asn Ser Lys Asn Thr Val Tyr

-continued

```
65                  70                  75                  80

Leu Gln Met Asn Ser Leu Arg Ala Glu Asp Thr Ala Val Tyr Tyr Cys
                85                  90                  95

Ala Arg Asp Pro Val Tyr Ala Thr Ser Ser Gly Tyr Phe Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 3
<211> LENGTH: 11
<212> TYPE: PRT
<213> ORGANISM: Artificial Sequence
```

<220> FEATURE:
<223> OTHER INFORMATION: CDR L1 of clone 16-22-H05?

<400> SEQUENCE: 3

Gln Ala Ser Gln Ser Ile Phe Ser Gly Leu Ala
1 5 10

<210> SEQ ID NO 4
<211> LENGTH: 7
<212> TYPE: PRT
<213> ORGANISM: Artificial Sequence
<220> FEATURE:
<223> OTHER INFORMATION: CDR L2 of clone 16-22-H05

<400> SEQUENCE: 4

Gly Ala Ser Lys Leu Ala Ser
1 5

<210> SEQ ID NO 5
<211> LENGTH: 15
<212> TYPE: PRT
<213> ORGANISM: Artificial Sequence
<220> FEATURE:
<223> OTHER INFORMATION: CDR L3 of clone 16-22-H05

<400> SEQUENCE: 5

Gln Ser Tyr Tyr Tyr Ser Ser Ser Ser Ser Asp Gly Ser Tyr Ala
1 5 10 15

<210> SEQ ID NO 6
<211> LENGTH: 10
<212> TYPE: PRT
<213> ORGANISM: Artificial Sequence
<220> FEATURE:
<223> OTHER INFORMATION: CDR H1 of clone 16-22-H05

<400> SEQUENCE: 6

Gly Ile Asp Phe Asn Asn Tyr Gly Ile Gly
1 5 10

<210> SEQ ID NO 7
<211> LENGTH: 17
<212> TYPE: PRT
<213> ORGANISM: Artificial Sequence
<220> FEATURE:
<223> OTHER INFORMATION: CDR H2 of clone 16-22-H05

<400> SEQUENCE: 7

Tyr Ile Tyr Pro Gly Phe Ala Ile Thr Asn Phe Ala Asn Ser Val Lys
1 5 10 15

Gly

<210> SEQ ID NO 8
<211> LENGTH: 13
<212> TYPE: PRT
<213> ORGANISM: Artificial Sequence
<220> FEATURE:
<223> OTHER INFORMATION: CDR H3 of clone 16-22-H05

<400> SEQUENCE: 8

Asp Pro Val Tyr Ala Thr Ser Ser Gly Tyr Phe Asp Leu
1 5 10

<210> SEQ ID NO 9
<211> LENGTH: 122
<212> TYPE: PRT

```
<213> ORGANISM: Artificial Sequence
<220> FEATURE:
<223> OTHER INFORMATION: VH of humanized IgG of clone 16-22-H05

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Asn Asn Tyr
            20                  25                  30

Gly Ile Gly Trp Val Arg Gln Ala Pro Gly Lys Gly Leu Glu Trp Ile
        35                  40                  45

Thr Tyr Ile Tyr Pro Gly Phe Ala Ile Thr Asn Phe Ala Asn Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Pro Val Tyr Ala Thr Ser Ser Gly Tyr Phe Asp Leu Trp
            100                 105                 110

Gly Gln Gly Thr Leu Val Thr Val Ser Ser
        115                 120


<210> SEQ ID NO 10
<211> LENGTH: 114
<212> TYPE: PRT
<213> ORGANISM: Artificial Sequence
<220> FEATURE:
<223> OTHER INFORMATION: VL of humanized IgG of clone 16-22-H05 ?

<400> SEQUENCE: 10

Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Ser Ile Phe Ser Gly
            20                  25                  30

Leu Ala Trp Tyr Gln Gln Lys Pro Gly Lys Ala Pro Lys Leu Leu Ile
        35                  40                  45

Tyr Gly Ala Ser Lys Leu Ala Ser Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Ala Asp Phe Ala Thr Tyr Tyr Cys Gln Ser Tyr Tyr Tyr Ser Ser Ser
                85                  90                  95

Ser Ser Asp Gly Ser Tyr Ala Phe Gly Gly Gly Thr Lys Leu Thr Val
            100                 105                 110

Leu Gly


<210> SEQ ID NO 11
<211> LENGTH: 451
<212> TYPE: PRT
<213> ORGANISM: Artificial Sequence
<220> FEATURE:
<223> OTHER INFORMATION: Heavy chain of Ab-YTE-DLE-PVAdeltaG (based on
      clone 16-22-H05)

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Asn Asn Tyr
            20                  25                  30
```

-continued

```
Gly Ile Gly Trp Val Arg Gln Ala Pro Gly Lys Gly Leu Glu Trp Ile
        35                  40                  45

Thr Tyr Ile Tyr Pro Gly Phe Ala Ile Thr Asn Phe Ala Asn Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Pro Val Tyr Ala Thr Ser Ser Gly Tyr Phe Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Pro Val Ala
225                 230                 235                 240

Gly Pro Asp Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Leu Pro Glu
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445
```

```
Pro Gly Lys
    450


<210> SEQ ID NO 12
<211> LENGTH: 451
<212> TYPE: PRT
<213> ORGANISM: Artificial Sequence
<220> FEATURE:
<223> OTHER INFORMATION: Heavy chain of Ab-A-DLE-PVAdeltaG (based on
      clone 16-22-H05)

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Asn Asn Tyr
            20                  25                  30

Gly Ile Gly Trp Val Arg Gln Ala Pro Gly Lys Gly Leu Glu Trp Ile
        35                  40                  45

Thr Tyr Ile Tyr Pro Gly Phe Ala Ile Thr Asn Phe Ala Asn Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Pro Val Tyr Ala Thr Ser Ser Gly Tyr Phe Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Pro Val Ala
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Leu Pro Glu
                325                 330                 335

Glu Lys Thr Ile Ser Lys Ala Lys Gly Gln Pro Arg Glu Pro Gln Val
            340                 345                 350
```

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Ala His Tyr Thr Gln Lys Ser Leu Ser Leu Ser
        435                 440                 445

Pro Gly Lys
    450

<210> SEQ ID NO 13
<211> LENGTH: 451
<212> TYPE: PRT
<213> ORGANISM: Artificial Sequence
<220> FEATURE:
<223> OTHER INFORMATION: Heavy chain of Ab-A-AEA-PVA?G (based on clone
      16-22-H05)

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Asn Asn Tyr
            20                  25                  30

Gly Ile Gly Trp Val Arg Gln Ala Pro Gly Lys Gly Leu Glu Trp Ile
        35                  40                  45

Thr Tyr Ile Tyr Pro Gly Phe Ala Ile Thr Asn Phe Ala Asn Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Pro Val Tyr Ala Thr Ser Ser Gly Tyr Phe Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Pro Val Ala
225                 230                 235                 240

Gly Pro Ser Val Phe Leu Phe Pro Pro Lys Pro Lys Asp Thr Leu Met

-continued

```
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Ala Ala Leu Pro Ala Pro Glu
                325                 330                 335

Ala Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Ala His Tyr Thr Gln Lys Ser Leu Ser Leu Ser
        435                 440                 445

Pro Gly Lys
    450


<210> SEQ ID NO 14
<211> LENGTH: 11
<212> TYPE: PRT
<213> ORGANISM: Artificial Sequence
<220> FEATURE:
<223> OTHER INFORMATION: CDR L1 of clone 17-22-B03

<400> SEQUENCE: 14

Gln Ala Ser Gln Ser Ile Ser Ser Tyr Leu Ala
1               5                   10


<210> SEQ ID NO 15
<211> LENGTH: 7
<212> TYPE: PRT
<213> ORGANISM: Artificial Sequence
<220> FEATURE:
<223> OTHER INFORMATION: CDR L2 of clone 17-22-B03

<400> SEQUENCE: 15

Lys Ala Ser Thr Leu Ala Ser
1               5


<210> SEQ ID NO 16
<211> LENGTH: 13
<212> TYPE: PRT
<213> ORGANISM: Artificial Sequence
<220> FEATURE:
<223> OTHER INFORMATION: CDR L3 of clone 17-22-B03

<400> SEQUENCE: 16

Gln Cys Thr Tyr Tyr Glu Pro Ser Tyr Val Phe Arg Ala
1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: CDR H1 of clone 17-22-B03

<400> SEQUENCE: 17

```
Gly Ile Asp Phe Ser Ala Gly Tyr Asp Met Cys
1               5                   10
```

<210> SEQ ID NO 18
<211> LENGTH: 17
<212> TYPE: PRT
<213> ORGANISM: Artificial Sequence
<220> FEATURE:
<223> OTHER INFORMATION: CDR H2 of clone 17-22-B03

<400> SEQUENCE: 18

```
Cys Ile Asp Ser Arg Arg Glu Glu Ser Asp Tyr Ala Ser Trp Ala Lys
1               5                   10                  15

Gly
```

<210> SEQ ID NO 19
<211> LENGTH: 14
<212> TYPE: PRT
<213> ORGANISM: Artificial Sequence
<220> FEATURE:
<223> OTHER INFORMATION: CDR H3 of clone 17-22-B03

<400> SEQUENCE: 19

```
Gly Gly Tyr Gly Gly Asp Gly Val Asp Gly Ala Phe Asp Pro
1               5                   10
```

<210> SEQ ID NO 20
<211> LENGTH: 124
<212> TYPE: PRT
<213> ORGANISM: Artificial Sequence
<220> FEATURE:
<223> OTHER INFORMATION: VH of humanized IgG of clone 17-22-B03

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Ser Ala Gly
            20                  25                  30

Tyr Asp Met Cys Trp Val Arg Gln Ala Pro Gly Lys Gly Leu Glu Trp
        35                  40                  45

Ile Ala Cys Ile Asp Ser Arg Arg Glu Glu Ser Asp Tyr Ala Ser Trp
    50                  55                  60

Ala Lys Gly Arg Phe Thr Ile Ser Lys Asp Ser Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Gly Gly Tyr Gly Gly Asp Gly Val Asp Gly Ala Phe Asp
            100                 105                 110

Pro Trp Gly Gln Gly Thr Leu Val Thr Val Ser Ser
        115                 120
```

<210> SEQ ID NO 21
<211> LENGTH: 112

-continued

```
<212> TYPE: PRT
<213> ORGANISM: Artificial Sequence
<220> FEATURE:
<223> OTHER INFORMATION: VL of humanized IgG of clone 17-22-B03?-(sc08)

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Tyr Glu Pro Ser
                85                  90                  95

Tyr Val Phe Arg Ala Phe Gly Gly Gly Thr Lys Leu Thr Val Leu Gly
            100                 105                 110


<210> SEQ ID NO 22
<211> LENGTH: 112
<212> TYPE: PRT
<213> ORGANISM: Artificial Sequence
<220> FEATURE:
<223> OTHER INFORMATION: VL of humanized IgG of clone 17-22-B03?-(sc02)

<400> SEQUENCE: 22

Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Pro
65                  70                  75                  80

Ala Asp Phe Ala Thr Tyr Tyr Cys Gln Cys Thr Tyr Tyr Glu Pro Ser
                85                  90                  95

Tyr Val Phe Arg Ala Phe Gly Gly Gly Thr Lys Leu Thr Val Leu Gly
            100                 105                 110


<210> SEQ ID NO 23
<211> LENGTH: 219
<212> TYPE: PRT
<213> ORGANISM: Artificial Sequence
<220> FEATURE:
<223> OTHER INFORMATION: Light chain of humanized IgG of clone
      17-22-B03?-(sc08)

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45
```

-continued

```
Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Tyr Glu Pro Ser
                85                  90                  95

Tyr Val Phe Arg Ala Phe Gly Gly Gly Thr Lys Leu Thr Val Leu Gly
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 24
<211> LENGTH: 219
<212> TYPE: PRT
<213> ORGANISM: Artificial Sequence
<220> FEATURE:
<223> OTHER INFORMATION: Light chain of humanized IgG of clone
      17-22-B03?-(sc02)

<400> SEQUENCE: 24

Asp Ile Gln Met Thr Gln Ser Pro Ser Ser Leu Ser Ala Ser Val Gly
1               5                   10                  15

Asp Arg Val Thr Ile Lys Cys Gln Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Pro
65                  70                  75                  80

Ala Asp Phe Ala Thr Tyr Tyr Cys Gln Cys Thr Tyr Tyr Glu Pro Ser
                85                  90                  95

Tyr Val Phe Arg Ala Phe Gly Gly Gly Thr Lys Leu Thr Val Leu Gly
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 25
<211> LENGTH: 453
<212> TYPE: PRT
<213> ORGANISM: Artificial Sequence
<220> FEATURE:
<223> OTHER INFORMATION: Heavy chain of Ab-YTE-DLE-PVAdeltaG (based on clone 17-22-B03)

<400> SEQUENCE: 25

Glu Val Gln Leu Val Glu Ser Gly Gly Gly Leu Val Gln Pro Gly Gly
1 5 10 15

Ser Leu Arg Leu Ser Cys Lys Ala Ser Gly Ile Asp Phe Ser Ala Gly
20 25 30

Tyr Asp Met Cys Trp Val Arg Gln Ala Pro Gly Lys Gly Leu Glu Trp
35 40 45

Ile Ala Cys Ile Asp Ser Arg Arg Glu Glu Ser Asp Tyr Ala Ser Trp
50 55 60

Ala Lys Gly Arg Phe Thr Ile Ser Lys Asp Ser Ser Lys Asn Thr Val
65 70 75 80

Tyr Leu Gln Met Asn Ser Leu Arg Ala Glu Asp Thr Ala Val Tyr Tyr
85 90 95

Cys Ala Arg Gly Gly Tyr Gly Gly Asp Gly Val Asp Gly Ala Phe Asp
100 105 110

Pro Trp Gly Gln Gly Thr Leu Val Thr Val Ser Ser Ala Ser Thr Lys
115 120 125

Gly Pro Ser Val Phe Pro Leu Ala Pro Ser Ser Lys Ser Thr Ser Gly
130 135 140

Gly Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Pro
225 230 235 240

Val Ala Gly Pro Asp Val Phe Leu Phe Pro Pro Lys Pro Lys Asp Thr
245 250 255

Leu Tyr Ile Thr Arg Glu Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Leu

-continued

```
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 26
<211> LENGTH: 453
<212> TYPE: PRT
<213> ORGANISM: Artificial Sequence
<220> FEATURE:
<223> OTHER INFORMATION: Heavy chain of Ab-A-DLE-PVAdeltaG (based on
      clone 17-22-B03)

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Ser Ala Gly
            20                  25                  30

Tyr Asp Met Cys Trp Val Arg Gln Ala Pro Gly Lys Gly Leu Glu Trp
        35                  40                  45

Ile Ala Cys Ile Asp Ser Arg Arg Glu Glu Ser Asp Tyr Ala Ser Trp
    50                  55                  60

Ala Lys Gly Arg Phe Thr Ile Ser Lys Asp Ser Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Gly Gly Tyr Gly Gly Asp Gly Val Asp Gly Ala Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220
```

-continued

```
Lys Ser Cys Asp Lys Thr His Thr Cys Pro Pro Cys Pro Ala Pro Pro
225                 230                 235                 240

Val Ala Gly Pro Asp Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Leu
                325                 330                 335

Pro Glu Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Ala His Tyr Thr Gln Lys Ser Leu Ser
        435                 440                 445

Leu Ser Pro Gly Lys
    450
```

<210> SEQ ID NO 27
<211> LENGTH: 453
<212> TYPE: PRT
<213> ORGANISM: Artificial Sequence
<220> FEATURE:
<223> OTHER INFORMATION: Heavy chain of Ab-A-AEA-PVAdeltaG (based on clone 17-22-B03)

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Lys Ala Ser Gly Ile Asp Phe Ser Ala Gly
            20                  25                  30

Tyr Asp Met Cys Trp Val Arg Gln Ala Pro Gly Lys Gly Leu Glu Trp
        35                  40                  45

Ile Ala Cys Ile Asp Ser Arg Arg Glu Glu Ser Asp Tyr Ala Ser Trp
    50                  55                  60

Ala Lys Gly Arg Phe Thr Ile Ser Lys Asp Ser Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Gly Gly Tyr Gly Gly Asp Gly Val Asp Gly Ala Phe Asp
            100                 105                 110

Pro Trp Gly Gln Gly Thr Leu Val Thr Val Ser Ser Ala Ser Thr Lys
        115                 120                 125
```

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Ala Ala Leu Pro Ala
                325                 330                 335

Pro Glu Ala Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Ala His Tyr Thr Gln Lys Ser Leu Ser
        435                 440                 445

Leu Ser Pro Gly Lys
    450

<210> SEQ ID NO 28
<211> LENGTH: 231
<212> TYPE: PRT
<213> ORGANISM: Artificial Sequence
<220> FEATURE:
<223> OTHER INFORMATION: Fc region of Ab-YTE-DLE-PVAdeltaG (including hinge region)

<400> SEQUENCE: 28

Glu Pro Lys Ser Cys Asp Lys Thr His Thr Cys Pro Pro Cys Pro Ala
1               5                   10                  15

Pro Pro Val Ala Gly Pro Asp Val Phe Leu Phe Pro Pro Lys Pro Lys

-continued

```
            20                  25                  30

Asp Thr Leu Tyr Ile Thr Arg Glu Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Leu Pro Glu Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230


<210> SEQ ID NO 29
<211> LENGTH: 231
<212> TYPE: PRT
<213> ORGANISM: Artificial Sequence
<220> FEATURE:
<223> OTHER INFORMATION: Fc region of Ab-A-DLE-PVAdeltaG (including
      hinge region)

<400> SEQUENCE: 29

Glu Pro Lys Ser Cys Asp Lys Thr His Thr Cys Pro Pro Cys Pro Ala
1               5                   10                  15

Pro Pro Val Ala Gly Pro Asp Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Leu Pro Glu Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140
```

-continued

Asn Gln Val Ser Leu Thr Cys Leu Val Lys Gly Phe Tyr Pro Ser Asp
145 150 155 160

Ile Ala Val Glu Trp Glu Ser Asn Gly Gln Pro Glu Asn Asn Tyr Lys
165 170 175

Thr Thr Pro Pro Val Leu Asp Ser Asp Gly Ser Phe Phe Leu Tyr Ser
180 185 190

Lys Leu Thr Val Asp Lys Ser Arg Trp Gln Gln Gly Asn Val Phe Ser
195 200 205

Cys Ser Val Met His Glu Ala Leu His Ala His Tyr Thr Gln Lys Ser
210 215 220

Leu Ser Leu Ser Pro Gly Lys
225 230

<210> SEQ ID NO 30
<211> LENGTH: 231
<212> TYPE: PRT
<213> ORGANISM: Artificial Sequence
<220> FEATURE:
<223> OTHER INFORMATION: Fc region of Ab-A-AEA-PVAdeltaG (including hinge region)

<400> SEQUENCE: 30

Glu Pro Lys Ser Cys Asp Lys Thr His Thr Cys Pro Pro Cys Pro Ala
1 5 10 15

Pro Pro Val Ala Gly Pro Ser Val Phe Leu Phe Pro Pro Lys Pro Lys
20 25 30

Asp Thr Leu Met Ile Ser Arg Thr Pro Glu Val Thr Cys Val Val Val
35 40 45

Asp Val Ser His Glu Asp Pro Glu Val Lys Phe Asn Trp Tyr Val Asp
50 55 60

Gly Val Glu Val His Asn Ala Lys Thr Lys Pro Arg Glu Glu Gln Tyr
65 70 75 80

Asn Ser Thr Tyr Arg Val Val Ser Val Leu Thr Val Leu His Gln Asp
85 90 95

Trp Leu Asn Gly Lys Glu Tyr Lys Cys Lys Val Ser Asn Ala Ala Leu
100 105 110

Pro Ala Pro Glu Ala Lys Thr Ile Ser Lys Ala Lys Gly Gln Pro Arg
115 120 125

Glu Pro Gln Val Tyr Thr Leu Pro Pro Ser Arg Glu Glu Met Thr Lys
130 135 140

Asn Gln Val Ser Leu Thr Cys Leu Val Lys Gly Phe Tyr Pro Ser Asp
145 150 155 160

Ile Ala Val Glu Trp Glu Ser Asn Gly Gln Pro Glu Asn Asn Tyr Lys
165 170 175

Thr Thr Pro Pro Val Leu Asp Ser Asp Gly Ser Phe Phe Leu Tyr Ser
180 185 190

Lys Leu Thr Val Asp Lys Ser Arg Trp Gln Gln Gly Asn Val Phe Ser
195 200 205

Cys Ser Val Met His Glu Ala Leu His Ala His Tyr Thr Gln Lys Ser
210 215 220

Leu Ser Leu Ser Pro Gly Lys
225 230

ANTIBODY VARIANTS

PRIORITY

This application corresponds to the U.S. National phase of International Application No. PCT/EP2018/074525, filed Sep. 11, 2018, which, in turn, claims priority to European Patent Application No. 17.191987.1 filed Sep. 19, 2017, the contents of which are incorporated by reference herein in their entirety.

SEQUENCE LISTING

This application contains a Sequence Listing that has been submitted in ASCII format via EFS-Web and is hereby incorporated by reference in its entirety. Said ASCII copy, created on Mar. 17, 2020, is named LNK_210US_SEQ_LISTING.txt and is 49,150 bytes in size.

FIELD OF THE INVENTION

The present invention relates to modified antibodies having improved resistance against proteolytic degradation and altered effector functions and/or pharmacokinetic properties. The antibodies are useful in the therapeutic treatment of various disorders, in particular of inflammatory conditions.

BACKGROUND

Monoclonal antibodies have gained increasing importance as therapeutic reagents in clinical medicine over the last 20 years. For many years, efforts to improve antibodies concentrated on reducing their potential immunogenicity, leading to humanized or even fully human antibodies. Another approach aims to optimize antibodies by improving their effector functions. While direct effects are mediated by the variable antigen binding region of the antibody, indirect effects are mediated by the constant Fc region. Efforts to improve effector functions mainly concentrate on modulating the Fc region. In addition, improving the serum half-life of therapeutic antibodies is desirable, which may reduce the amount of required antibodies, and may increase their convenience for patients by prolonging treatment intervals.

For therapeutic applications, immunoglobulin G (IgG) has been the preferred class of choice for several reasons; IgGs are easy to purify, are relatively stable on storage, can be administered intravenously, have extended biological half-life in vivo and are able to engage a range of biological effector functions such as activation of complement dependent cytotoxicity (CDC) and recruitment of effector cells through various Fc-receptor interactions (antibody-dependent cellular cytotoxicity; ADCC). Of the five immunoglobulin classes, IgG exhibits the longest biological half-life due to its unique interaction with the IgG recycling receptor, the neonatal Fc receptor (FcRn). One of the known functions of the receptor is to rescue IgG from catalytic degradation. A solved FcRn-Fc cocrystal structure has shown that the interaction with Fc occurs in the IgG hinge-$C_H2$-$C_H3$ region. This interaction occurs in a strictly pH-dependent manner at acidic pH of 6.0-6.5 in the endosomes. Bound IgG molecules are recycled back to the cell surface where they are released at physiological pH of 7.4 into the circulation, whereas noncomplexed IgG molecules are destined for lysosomal degradation. This recycling is the mechanism for the extended half-life of IgG; modulation of the FcRn-IgG interaction will therefore allow specific control of the serum half-lives of gamma immunoglobulins and Fc-fusion proteins.

Depending on the application it may be desirable to increase or reduce the serum residence time of IgG. For therapeutic application a longer half-life is desirable as smaller doses and fewer injections will be required. Several approaches to increase the half-life have been investigated including the use of polyethylene glycol (PEG), generation of albumin- or Fc-fusion proteins and strengthening the FcRn-IgG interaction. PEGylated pharmaceuticals have been in the clinic since 1990 and PEGylation is an established technology for extension of drug residence in the blood. Since human serum albumin (HSA) is also recycled by FcRn via a pH-dependent interaction, several albumin-fusion proteins to enhance stability and half-life have also been produced. Additionally, antibody fragments fused to albumin or albumin-binding domains have demonstrated prolonged serum residence time in preclinical studies. The generation of Fc-fusion proteins is another strategy that will endow proteins or peptides with properties similar to an intact antibody.

Modifications of the Fc region that have been investigated are summarized in Saxena (2016) Frontiers in Immunology, Vol. 7, Article 580. Various Fc mutations are further described in WO 1998/023289 A1, WO 2000/042072 A2, WO 2010/106180 A2 and WO 2014/108198 A1.

WO 2012/087746 A1 and Kinder et al. (2013) The Journal Of Biological Chemistry Vol. 288, No. 43, pp. 30843-30854 investigated various mutations in the Fc region of an antibody for improving the resistance to proteolytic degradation.

There is an ongoing need for antibodies having improved effector functions, pharmacokinetics and/or resistance to proteolytic degradation.

SUMMARY OF THE INVENTION

The inventors of this application found that a combination of specific mutations in the Fc region of an antibody confer favorable properties to the antibody, including improved resistance to proteolytic degradation and increased affinity to FcRn at pH 6. Antibodies having the mutations have improved pharmacokinetic properties. In addition, the antibodies exhibit superior effector functions as compared to non-modified antibodies and/or known antibodies such as infliximab (IFX).

The present invention therefore relates to the subject matter defined in the following items [1] to [100]:

[1] An antibody comprising a TNFα-binding domain and an FcRn binding site, wherein the amino acid sequence of the antibody comprises (i) the amino acids 233P, 234V, 235A, and a deletion at amino acid position 236; and (ii) the amino acid 434A or the amino acids 252Y, 254T and 256E.

[2] The antibody of item [1], wherein the antibody is a modified antibody having the substitutions E233P, L234V and L235A and a deletion of G236.

[3] The antibody of item [2], wherein the antibody further has the substitution N434A.

[4] The antibody of item [2], wherein the antibody further has the substitutions M252Y, S254T and T256E.

[5] The antibody of any one of the preceding items, wherein the amino acid sequence of the antibody further comprises the amino acids 239D, 330L and 332E.

[6] The antibody of item [5], wherein the antibody is a modified antibody having the substitutions S239D, A330L and I332E.

[7] The antibody of item [1], wherein the amino acid sequence of the antibody comprises the amino acids 233P, 234V, 235A, 239D, 330L, 332E and 434A, and a deletion at amino acid position 236.

[8] The antibody of item [7], wherein the antibody is a modified antibody having the substitutions E233P, L234V, L235A, S239D, A330L, I332E and N434A, and a deletion of G236.

[9] The antibody of item [7] or [8], comprising the amino acid sequence as shown in SEQ ID NO:29.

[10] The antibody of item [1], wherein the amino acid sequence of the antibody comprises the amino acids 233P, 234V, 235A, 239D, 330L, 332E, 252Y, 254T and 256E, and a deletion at amino acid position 236.

[11] The antibody of item [10], wherein the antibody is a modified antibody having the substitutions E233P, L234V, L235A, S239D, A330L, I332E, M252Y, S254T and T256E, and a deletion of G236.

[12] The antibody of item [10] or [11], comprising the amino acid sequence as shown in SEQ ID NO:28.

[13] The antibody of item [1], wherein the amino acid sequence of the antibody comprises the amino acids 233P, 234V, 235A, 326A, 332E, 333A and 434A, and a deletion at amino acid position 236.

[14] The antibody of item [13], wherein the antibody is a modified antibody having the substitutions E233P, L234V, L235A, K326A, I332E, E333A and N434A and a deletion of G236.

[15] The antibody of item [13] or [14], comprising the amino acid sequence as shown in SEQ ID NO:30.

[16] The antibody of any one of the preceding items, having an affinity to human FcRn at pH 6 that is greater than that of infliximab.

[17] The antibody of any one of the preceding items, having an affinity to human FcRn at pH 6 that is characterized by a dissociation constant $K_D$ of less than 500 nM.

[18] The antibody of any one of the preceding items, having an affinity to human FcRn at pH 6 that is characterized by a dissociation constant $K_D$ of less than 400 nM.

[19] The antibody of any one of the preceding items, having an affinity to human FcRn at pH 6 that is characterized by a dissociation constant $K_D$ of less than 300 nM.

[20] The antibody of any one of the preceding items, having an affinity to human FcRn at pH 6 that is characterized by a dissociation constant $K_D$ of less than 200 nM.

[21] The antibody of any one of the preceding items, having an affinity to human FcRn at pH 6 that is characterized by a dissociation constant $K_D$ in the range from 5 nM to 500 nM, or from 10 nM to 400 nM, or from 25 nM to 300 nM, or from 50 nM to 200 nM, or from 75 nM to 175 nM.

[22] The antibody of any one of the preceding items, wherein said $K_D$ characterizing the affinity to human FcRn at pH 6 is determined by surface plasmon resonance (SPR).

[23] The antibody of any one of the preceding items, having an affinity to human FcRn at pH 7.4 that is characterized by a dissociation constant $K_D$ of greater than 10 μM.

[24] The antibody of any one of the preceding items, wherein said $K_D$ characterizing the affinity to human FcRn at pH 7.4 is determined by surface plasmon resonance (SPR).

[25] The antibody of any one of items [1] to [22], wherein its affinity to human FcRn at pH 7.4 is so low that a $K_D$ value cannot be determined by SPR.

[26] The antibody of any one of the preceding items, which binds to human TNFα with a $K_D$ of less than 200 μM.

[27] The antibody of any one of the preceding items, which binds to human TNFα with a $K_D$ of less than 100 μM.

[28] The antibody of any one of the preceding items, which binds to human TNFα with a $K_D$ of less than 50 μM.

[29] The antibody of any one of the preceding items, which binds to human TNFα with a $K_D$ of less than 25 μM.

[30] The antibody of any one of the preceding items, which binds to human TNFα with a $K_D$ of less than 10 μM.

[31] The antibody of any one of the preceding items, which is transported across a polarized cell monolayer from the apical side to the basolateral side.

[32] The antibody of any one of the preceding items, which is transported across a polarized cell monolayer from the apical side to the basolateral side in greater amount than a control antibody comprising a light chain having the amino acid sequence as shown in SEQ ID NO:1 and a heavy chain having the amino acid sequence as shown in SEQ ID NO:2.

[33] The antibody of any one of the preceding items, which is transported across a polarized cell monolayer from the apical side to the basolateral side in greater amount than infliximab.

[34] The antibody of item [32] or [33], wherein said amount refers to the mass of antibody transported across the polarized cell monolayer within four hours.

[35] The antibody of any one of items [31] to [34], wherein the amount of antibody transported across the polarized cell monolayer is greater than two times the amount of a parent immunoglobulin transported across the polarized cell monolayer, wherein said parent immunoglobulin differs from said antibody only in that its Fc region has only wild type amino acids.

[36] The antibody of any one of the preceding items, wherein a greater percentage of the antibody than that of infliximab is transported across a polarized cell monolayer from the apical side to the basolateral side in the presence of a tenfold excess of competing immunoglobulins, wherein the percentage refers to the total mass of immunoglobulins transported across the polarized cell monolayer.

[37] The antibody of item [36], wherein the percentage of the antibody transported across the polarized cell monolayer is greater than two times the percentage of a parent immunoglobulin transported across the polarized cell monolayer, wherein said parent immunoglobulin differs from said antibody only in that its Fc region has only wild type amino acids.

[38] The antibody of any one of items [31] to [37], wherein said polarized cell monolayer is a monolayer of polarized T84 cells.

[39] The antibody of any one of the preceding items, binding to CD16a(V) with a $K_D$ of less than 500 nM, or less than 300 nM, or less than 200 nM, or less than 100 nM.

[40] The antibody of any one of the preceding items, binding to CD16a(F) with a $K_D$ of less than 10 μM, or less than 1 μM.

[41] The antibody of any one of the preceding items, binding to CD16b(NA2) with a $K_D$ of less than 10 μM, or less than 5 μM, or less than 1 μM.

[42] The antibody of any one of the preceding items, having antibody-dependent cellular cytotoxicity (ADCC).

[43] The antibody of any one of the preceding items, capable of inducing $CD14^+CD206^+$ macrophages.

[44] The antibody of any one of the preceding items, capable of inducing $CD14^+CD206^+$ macrophages at a level equal to or greater than infliximab.

[45] The antibody of any one of the preceding items, capable of suppressing T-cell proliferation.

[46] The antibody of any one of the preceding items, capable of suppressing T-cell proliferation at a degree equal to or greater than infliximab.

[47] The antibody of any one of the preceding items, which is a non-fucosylated antibody or an antibody with reduced fucosylation.

[48] The antibody of any one of the preceding items, comprising (i) a $V_L$ domain comprising a CDR1 region having the amino acid sequence as shown in SEQ ID NO:3, a CDR2 region having the amino acid sequence as shown in SEQ ID NO:4, and a CDR3 region having the amino acid sequence as shown in SEQ ID NO:5, and (ii) a $V_H$ domain comprising a CDR1 region having the amino acid sequence as shown in SEQ ID NO:6, a CDR2 region having the amino acid sequence as shown in SEQ ID NO:7, and a CDR3 region having the amino acid sequence as shown in SEQ ID NO:8.

[49] The antibody of any one of the preceding items, comprising a $V_H$ domain having the amino acid sequence as shown in SEQ ID NO:9 and a $V_L$ domain having an amino acid sequence as shown in SEQ ID NO:10.

[50] The antibody of any one of the preceding items, comprising a light chain having the amino acid sequence as shown in SEQ ID NO:1 and a heavy chain having the amino acid sequence as shown in SEQ ID NO:11, SEQ ID 12, or SEQ ID NO:13.

[51] The antibody of any one of items [1] to [47], wherein said antibody comprises (i) a $V_L$ domain comprising a CDR1 region having the amino acid sequence as shown in SEQ ID NO:14, a CDR2 region having the amino acid sequence as shown in SEQ ID NO:15, and a CDR3 region having the amino acid sequence as shown in SEQ ID NO:16, and (ii) a $V_H$ domain comprising a CDR1 region having the amino acid sequence as shown in SEQ ID NO:17, a CDR2 region having the amino acid sequence as shown in SEQ ID NO:18, and a CDR3 region having the amino acid sequence as shown in SEQ ID NO:19.

[52] The antibody of item [51], comprising a $V_H$ domain having the amino acid sequence as shown in SEQ ID NO:20 and a $V_L$ domain having an amino acid sequence as shown in SEQ ID NO:21 or SEQ ID NO:22.

[53] The antibody of item [51] or [52], comprising a light chain having the amino acid sequence as shown in SEQ ID NO:23 or SEQ ID NO:24 and a heavy chain having the amino acid sequence as shown in SEQ ID NO:25, SEQ ID NO:26 or SEQ ID NO:27.

[54] The antibody of any one of the preceding items, wherein said antibody specifically binds to human TNFα.

[55] The antibody of any one of the preceding items, wherein said antibody does not significantly bind to TNFβ.

[56] The antibody of any one of the preceding items, wherein said antibody (i) binds to human TNFα with a dissociation constant ($K_D$) of less than 125 μM;

(ii) is cross-reactive with *Macaca mulatta* TNFα and with *Macaca fascicularis* TNFα;

(iii) has a greater potency than infliximab, as determined by an L929 assay; and/or (iv) is capable of binding to human $TNF\alpha_{Trimer}$ in a stoichiometry (antibody: $TNF\alpha_{Trimer}$) of at least 2.

[57] The antibody of any one of the preceding items, which binds to TNFα from *Macaca mulatta* with a $K_D$ of less than 1 nM.

[58] The antibody of any one of the preceding items, which binds to TNFα from *Macaca fascicularis* with a $K_D$ of less than 1 nM.

[59] The antibody of any one of the preceding items, wherein the potency of the antibody to inhibit TNFα-induced apoptosis relative to that of infliximab (relative potency), determined in an L929 assay, is greater than 3, and wherein said relative potency is the ratio of the $IC_{50}$ value in ng/mL of infliximab in the L929 assay to the $IC_{50}$ value in ng/mL of the antibody in the L929 assay.

[60] The antibody of any one of the preceding items, wherein the melting temperature of the variable domain of the antibody in scFv format, determined by differential scanning fluorimetry, is at least 65° C.

[61] The antibody of any one of the preceding items, wherein the melting temperature of the variable domain of the antibody in scFv format, determined by differential scanning fluorimetry, is at least 68° C.

[62] The antibody of any one of the preceding items, wherein the melting temperature, determined by differential scanning fluorimetry, is at least 70° C.

[63] The antibody of any one of the preceding items, wherein the antibody is capable of blocking the interaction between human TNFα and TNF receptor I (TNFRI).

[64] The antibody of any one of the preceding items, wherein the antibody is capable of blocking the interaction between human TNFα and TNF receptor II (TNFRII).

[65] The antibody of any one of the preceding items, which is capable of inhibiting cell proliferation of peripheral blood mononuclear cells in a mixed lymphocyte reaction.

[66] The antibody of any one of the preceding items, which is capable of inhibiting LPS-induced secretion of interleukin-1β from $CD14^+$ monocytes.

[67] The antibody of item [66], wherein the $IC_{50}$ value for inhibiting LPS-induced secretion of interleukin-1β is less than 1 nM.

[68] The antibody of item [67], wherein said $IC_{50}$ value for inhibiting LPS-induced secretion of interleukin-1β, on a molar basis, is lower than that of adalimumab.

[69] The antibody of any one of the preceding items, which is capable of inhibiting LPS-induced secretion of TNFα from $CD14^+$ monocytes.

[70] The antibody of item [69], wherein the $IC_{50}$ value for inhibiting LPS-induced secretion of TNFα is less than 1 nM.

[71] The antibody of item [70], wherein said $IC_{50}$ value for inhibiting LPS-induced secretion of TNFα, on a molar basis, is lower than that of adalimumab.

[72] The antibody of any one of the preceding items, which is an immunoglobulin G (IgG), preferably an IgG1.

[73] The antibody of any one of the preceding items, which is more resistant to proteolytic degradation than a wildtype antibody.

[74] The antibody of item [73], wherein said wildtype antibody is infliximab.

[75] The antibody of item [73], wherein said wildtype antibody is an immunoglobulin which differs from said antibody only in that its Fc region has only wild type amino acids.

[76] The antibody of item [73], wherein said wildtype antibody comprises a light chain having the amino acid sequence as shown in SEQ ID NO:1 and a heavy chain having the amino acid sequence as shown in SEQ ID NO:2.

[77] The antibody of any one items [73] to [76], wherein said proteolytic degradation includes degradation by matrix metalloproteinase 3 (MMP-3).

[78] The antibody of any one items [73] to [77], wherein said proteolytic degradation includes degradation by immunoglobulin G-degrading enzyme of *S. pyogenes* (IdeS).

[79] The antibody of any one items [73] to [78], wherein said proteolytic degradation includes degradation by Endoproteinase Glu-C from *Staphylococcus aureus* strain V8 (GluC).

[80] A nucleic acid encoding the antibody of any one of the preceding items.

[81] A vector or plasmid comprising the nucleic acid of item [80].

[82] A cell comprising the nucleic acid of item [80] or the vector or plasmid of item [81].

[83] A method of preparing the antibody of any one of items [1] to [79], comprising culturing the cell of item [82] in a medium under conditions that allow expression of the nucleic acid encoding the antibody, and recovering the antibody from the cells or from the medium.

[84] The antibody as defined in any one of items [1] to [79] for use in a method of treating an inflammatory disorder or a TNFα-related disorder.

[85] The antibody for use according to item [84], wherein said inflammatory disorder is selected from the list of diseases and disorders listed in Section "Disorders to be treated" below.

[86] The antibody for use according to item [84], wherein said inflammatory disorder is an inflammatory disorder of the gastrointestinal tract.

[87] The antibody for use according to item [86], wherein said inflammatory disorder of the gastrointestinal tract is inflammatory bowel disease.

[88] The antibody for use according to item [86] or [87], wherein said inflammatory disorder of the gastrointestinal tract is Crohn's disease.

[89] The antibody for use according to item [88], wherein said Crohn's disease is selected from the group consisting of ileal, colonic, ileocolonic, and/or isolated upper Crohn's disease (gastric, duodenal and/or jejunal) and including non-stricturing/non-penetrating, stricturing, penetrating and perianal disease behavior, allowing any combination of localization and disease behavior of any of the above mentioned.

[90] The antibody for use according to item [86] or [87], wherein said inflammatory disorder of the gastrointestinal tract is ulcerative colitis.

[91] The antibody for use according to item [90], wherein said ulcerative colitis is selected from the group consisting of ulcerative proctitis, sigmoiditis, proctosigmoiditis, left-sided colitis, pan-ulcerative colitis, and pouchitis.

[92] The antibody for use according to item [86] or [87], wherein said inflammatory disorder of the gastrointestinal tract is microscopic colitis.

[93] The antibody for use according to item [84], wherein said inflammatory disorder is arthritis.

[94] The antibody for use according to item [84] or [93], wherein said inflammatory disorder rheumatoid arthritis.

[95] The antibody for use according to any one of items [84] to [94], wherein said method comprises orally administering the antibody to a subject.

[96] The antibody for use according to any one of items [84] to [94], wherein said method comprises topically applying the antibody.

[97] A pharmaceutical composition comprising the antibody of any one of items [1] to [79].

[98] A method for improving the transcytosis of an antibody directed against TNFα, comprising introducing the substitutions E233P, L234V and L235A, deleting G236 and introducing the following further substitution(s) (a) or (b):

(a) M252Y, S254T and T256E (b) N434A;

and optionally further introducing one or more of the other substitutions described herein.

[99] A method for extending the plasma half-life of an antibody directed against TNFα, comprising introducing the substitutions E233P, L234V and L235A, deleting G236 and introducing the following further substitution(s) (a) or (b):

(a) M252Y, S254T and T256E (b) N434A;

and optionally further introducing one or more of the other substitutions described herein.

[100] A method of improving the resistance against proteolytic degradation of an antibody directed against TNFα, comprising introducing the substitutions E233P, L234V and L235A, deleting G236 and introducing the following further substitution(s) (a) or (b):

(a) M252Y, S254T and T256E (b) N434A;

and optionally further introducing one or more of the other substitutions described herein.

DETAILED DESCRIPTION

Figure 1:
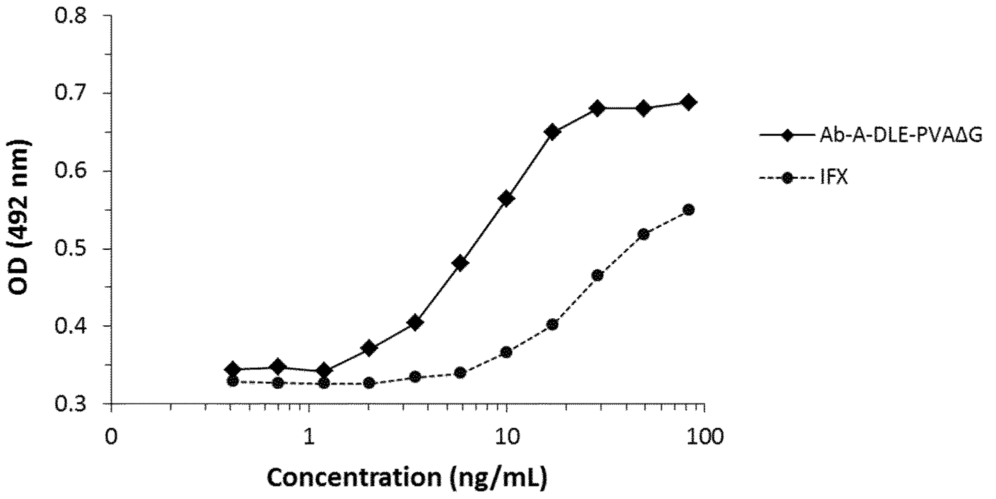
FIG. 1: Potency of anti-TNFα antibody variants to neutralize human TNFα in the L929 assay. Dose response curves for TNFα antibody variants and the reference infliximab are shown.
Figure 1:
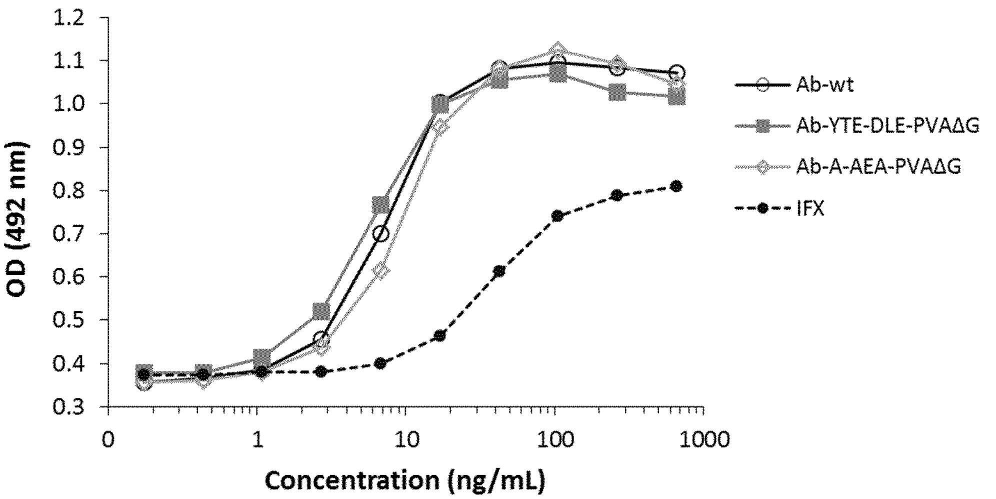

The present invention relates to an antibody that is capable of binding to TNFα and comprises a modified Fc region. The antibody has improved resistance to proteolytic degradation. The antibody further has a high affinity to human FcRn at pH 6 and low affinity to human FcRn at pH 7.4. The amino acid sequence of the antibody comprises the amino acids 233P, 234V, 235A, and a deletion at amino acid position 236 (EU numbering). The antibody further comprises either the amino acid 434A or the amino acids 252Y, 254T and 256E (EU numbering).

Throughout the present specification and claims, the Kabat numbering system is generally used when referring to a residue in the variable domain (approximately, residues 1-107 of the light chain and residues 1-113 of the heavy chain) (Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., *Sequences of Proteins of Immunological Interest,* 5th Ed. Public Health Service, National Institutes of Health, Bethesda, Md. (1991) expressly incorporated herein by reference). Unless stated otherwise herein, references to residues numbers in the variable domain of antibodies means residue numbering by the Kabat numbering system. Unless stated otherwise herein, references to residue numbers in the constant domain of antibodies means residue numbering by the EU numbering system (see e.g., WO 2006/073941).

Antibody

In the context of the present application, the term "antibody" is used as a synonym for "immunoglobulin" (Ig), which is defined as a protein belonging to the class IgG, IgM, IgE, IgA, or IgD (or any subclass thereof), and includes all conventionally known antibodies and functional fragments thereof. In the context of the present invention, a "functional fragment" of an antibody/immunoglobulin is defined as antigen-binding fragment or other derivative of a parental antibody that essentially maintains one or more of the properties of such parental antibody. An "antigen-binding fragment" or "antigen-binding domain" of an antibody/immunoglobulin is defined as fragment (e.g., a variable region of an IgG) that retains the antigen-binding region. An "antigen-binding region" of an antibody typically is found in one or more hypervariable region(s) of an antibody, i.e., the CDR-1, -2, and/or -3 regions. The antibodies of the present invention may be part of bi- or multifunctional constructs.

Preferably the antibody is a monoclonal antibody. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technologies, or a combination thereof. (Harlow and Lane, "Antibodies, A Laboratory Manual" CSH Press 1988, Cold Spring Harbor N.Y.).

In other embodiments, including embodiments relating to the in vivo use of the anti-TNFα antibodies in humans, chimeric, primatized, humanized, or human antibodies can be used. In a preferred embodiment, the antibody is a human antibody or a humanized antibody, more preferably a monoclonal human antibody or a monoclonal humanized antibody.

In another particular embodiment the antibody of the invention is an immunoglobulin, preferably an immunoglobulin G (IgG). The subclass of the IgG of the invention is not limited and includes $IgG_1$, $IgG_2$, $IgG_3$, and $IgG_4$. Preferably, the IgG of the invention is of subclass 1, 2 or 4, i.e. it is an $IgG_1$, $IgG_2$, or $IgG_4$ molecule, respectively. Most preferably, the IgG of the invention is of subclass 1, i.e. it is an $IgG_1$ molecule.

TNFα-Binding Domain

The TNFα-binding domain of the antibody of the invention is not particularly limited. It can be derived from any antibody that is capable of binding to TNFα.

Preferably, the antibody of the invention specifically binds to TNFα. As used herein, an antibody "specifically recognizes", or "specifically binds to" human TNFα, when the antibody is able to discriminate between human TNFα and one or more reference molecule(s). Preferably, the $IC_{50}$ value for binding to each of the reference molecules is at least 1,000 times greater than the IC50 value for binding to TNFα. In its most general form (and when no defined reference is mentioned), "specific binding" is referring to the ability of the antibody to discriminate between human TNFα and an unrelated biomolecule, as determined, for example, in accordance with a specificity assay methods known in the art. Such methods comprise, but are not limited to, Western blots and ELISA tests. For example, a standard ELISA assay can be carried out. Typically, determination of binding specificity is performed by using not a single reference biomolecule, but a set of about three to five unrelated biomolecules, such as milk powder, BSA, transferrin or the like. In one embodiment, specific binding refers to the ability of the antibody to discriminate between human TNFα and human TNFβ.

The antibody of the invention comprises a $V_L$ domain and a $V_H$ domain. The $V_L$ domain comprises a CDR1 region (CDRL1), a CDR2 region (CDRL2), a CDR3 region (CDRL3) and Framework regions. The $V_H$ domain comprises a CDR1 region (CDRH1), a CDR2 region (CDRH2), a CDR3 region (CDRH3) and Framework regions.

The term "CDR" refers to one of the six hypervariable regions within the variable domains of an antibody that mainly contribute to antigen binding. One of the most commonly used definitions for the six CDRs was provided by Kabat E. A. et al., (1991) Sequences of proteins of immunological interest. NIH Publication 91-3242). As used herein, Kabat's definition of CDRs only apply for CDR1, CDR2 and CDR3 of the light chain variable domain (CDR L1, CDR L2, CDR L3, or L1, L2, L3), as well as for CDR2 and CDR3 of the heavy chain variable domain (CDR H2, CDR H3, or H2, H3). CDR1 of the heavy chain variable domain (CDR H1 or H1), however, as used herein is defined by the following residues (Kabat numbering): It starts with position 26 and ends prior to position 36.

In a particular embodiment, the antibody of the invention comprises (i) a $V_L$ domain comprising a CDR1 region having the amino acid sequence as shown in SEQ ID NO:3, a CDR2 region having the amino acid sequence as shown in SEQ ID NO:4, and a CDR3 region having the amino acid sequence as shown in SEQ ID NO:5, and (ii) a $V_H$ domain comprising a CDR1 region having the amino acid sequence as shown in SEQ ID NO:6, a CDR2 region having the amino acid sequence as shown in SEQ ID NO:7, and a CDR3 region having the amino acid sequence as shown in SEQ ID NO:8.

In a more preferred embodiment, the antibody of the invention of the invention comprises a $V_H$ domain having the amino acid sequence as shown in SEQ ID NO:9. In another more preferred embodiment the antibody comprises a $V_L$ domain having the amino acid sequence as shown in SEQ ID NO:10. Most preferably, the antibody of the invention comprises (i) a $V_H$ domain having the amino acid sequence as shown in SEQ ID NO:9, and (ii) a $V_L$ domain having the amino acid sequence as shown in SEQ ID NO:10.

In another particular embodiment, the antibody of the invention comprises (i) a $V_L$ domain comprising a CDR1 region having the amino acid sequence as shown in SEQ ID NO:14, a CDR2 region having the amino acid sequence as shown in SEQ ID NO:15, and a CDR3 region having the amino acid sequence as shown in SEQ ID NO:16, and (ii) a $V_H$ domain comprising a CDR1 region having the amino acid sequence as shown in SEQ ID NO:17, a CDR2 region having the amino acid sequence as shown in SEQ ID NO:18, and a CDR3 region having the amino acid sequence as shown in SEQ ID NO:19.

In a more preferred embodiment, the antibody of the invention of the invention comprises a $V_H$ domain having the amino acid sequence as shown in SEQ ID NO:20. In another more preferred embodiment the antibody comprises a $V_L$ domain having the amino acid sequence as shown in SEQ ID NO:21 or SEQ ID NO:22. Most preferably, the antibody of the invention comprises (i) a $V_H$ domain having the amino acid sequence as shown in SEQ ID NO:21, and (ii) a $V_L$ domain having the amino acid sequence as shown in SEQ ID NO:21 or SEQ ID NO:22.

The antibody of the invention has a high affinity to human TNFα. The term "$K_D$," refers to the dissociation equilibrium constant of a particular antibody-antigen interaction. Typically, the antibody of the invention binds to human TNFα with a dissociation equilibrium constant ($K_D$) of less than approximately $2\times10^{-10}$ M, preferably less than $1.5\times10^{-10}$ M, preferably less than $1.25\times10^{-10}$ M, more preferably less than $1\times10^{-10}$ M, most preferably less than $7.5\times10^{-11}$ M or even less than $5\times10^{-11}$ M, as determined using surface plasmon resonance (SPR) technology in a BIACORE instrument. In particular, the determination of the $K_D$ is carried out as described in Example 1.

Modifications of the Fc Region

A "modified Fc region" comprises an amino acid sequence which differs from that of a native sequence Fc region by virtue of at least one "amino acid modification" or "mutation" as herein defined. Preferably, the modified Fc region comprises a modified FcRn binding site which has at least one amino acid substitution compared to a native sequence FcRn binding site or to the FcRn binding site of a parent antibody, e.g. from about one to about ten amino acid substitutions, and preferably from about one to about five amino acid substitutions in a native sequence FcRn binding site or in the FcRn binding site of the parent antibody. Alternatively, the antibody may have a modification outside the FcRn binding site which affects the affinity to FcRn, e.g. by structural changes. Typically, the affinity to human FcRn at pH 6 is increased due to the modification. It is preferred that the affinity to human FcRn at pH 7.4 is not substantially affected by the modification. The modifications can be generated by methods that are known per se, e.g. by site-directed mutagenesis as described in "Antibody Engineering—Methods and Protocols", edited by Patrick Chames, $2^{nd}$ ed., 2012, Chapter 31 (ISBN 978-1-61779-973-0).

The amino acid sequence of the antibody of the invention comprises the amino acid proline at position 233, the amino acid valine at position 234, and the amino acid alanine at position 235, and further has a deletion of the amino acid at position 236 (EU numbering). This is referred to as "233P/234V/235A/236del" herein. The native amino acid at position 233 of non-modified human IgG antibodies is glutamic acid (E). The native amino acid at position 234 of non-modified human IgG antibodies is leucine (L). The native amino acid at position 235 of non-modified human IgG antibodies is leucine (L). The native amino acid at position 236 of non-modified human IgG antibodies is glycine (G). Thus, the antibody of the invention can be obtained by introducing the mutations E233P, L234V, L235A and G236del into an antibody. This is referred to as E233P/L234V/L235A/G236del herein. Preferably, the antibody of the invention is obtainable or obtained by substituting proline for glutamic acid at position 233, substituting valine for leucine at position 234, substituting alanine for leucine at position 235, and deleting glycine at position 236.

The amino acid sequence of the antibody of the invention further comprises (i) the amino acid alanine at position 434, or (ii) the amino acid tyrosine at position 252, the amino acid threonine at position 254 and the amino acid glutamic acid at position 256. This is referred to as 434A and 252Y/254T/256E herein, respectively. The native amino acid at position 434 of non-modified human IgG antibodies is asparagine (N). The native amino acid at position 252 of non-modified human IgG antibodies is methionine (M). The native amino acid at position 254 of non-modified human IgG antibodies is serine (S). The native amino acid at position 256 of non-modified human IgG antibodies is threonine (T). Thus, the antibody of the invention can be obtained by introducing the further mutation(s) N434A or M252Y/S254T/T256E into an antibody.

That is, the amino acid sequence of the antibody of the invention comprises 233P/234V/235A/236del/434A or 233P/234V/235A/236del/252Y/254T/256E. This amino acid sequence can be obtained by introducing the mutations E233P/L234V/L235A/G236del/N434A or E233P/L234V/L235A/G236del/M252Y/S254T/T256E into an amino acid sequence of an antibody, e.g. of an antibody the Fc region of which has a non-modified or wild-type amino acid sequence.

The remaining amino acid sequence of the Fc region may be identical to the native amino acid sequence of a typical human IgG. It is possible, however, that the amino acid sequence of the antibody comprises one or more additional mutations or substitutions to the native amino acid sequence of the Fc region of a native antibody, as long as the antibody still has TNFα-binding activity, FcRn binding activity at pH 6.0 and one or more effector functions.

In a preferred embodiment, the antibody of the invention has at least one, or at least two, or at least three additional substitutions. In one embodiment, the amino acid sequence of the antibody has the amino acids 239D/330L/332E, preferably obtainable or obtained by introducing the substitutions S239D/A330L/I332E. In another embodiment, the amino acid sequence of the antibody has the amino acids 326A/332E/333A, preferably obtainable or obtained by introducing the substitutions K326A/I332E/E333A.

In a preferred embodiment, the amino acid sequence of the antibody of the invention comprises 233P/234V/235A/236del/239D/330L/332E/434A. This antibody can be obtained by introducing the mutations E233P/L234V/L235A/236del/S239D/A330L/I332E/N434A into an amino acid sequence of an antibody, e.g. of an antibody the Fc region of which has a non-modified or wild-type amino acid sequence.

In another preferred embodiment, the amino acid sequence of the antibody of the invention comprises 233P/234V/235A/236del/239D/330L/332E/252Y/254T/256E. This antibody can be obtained by introducing the mutations E233P/L234V/L235A/236del/S239D/A330L/I332E/M252Y/S254T/T256E into an amino acid sequence of an antibody, e.g. of an antibody the Fc region of which has a non-modified or wild-type amino acid sequence.

In another preferred embodiment, the amino acid sequence of the antibody of the invention comprises 233P/234V/235A/236del/326A/332E/333A/434A. This antibody can be obtained by introducing the mutations E233P/L234V/L235A/236del/K326A/I332E/E333A/N434A into an amino acid sequence of an antibody, e.g. of an antibody the Fc region of which has a non-modified or wild-type amino acid sequence.

In a preferred embodiment, the Fc region of the antibody of the invention, including the hinge region, comprises or consists of the amino acid sequence selected from the group consisting of SEQ ID NO:28, SEQ ID NO:29 and SEQ ID NO:30.

In one embodiment, the heavy chain of the antibody of the invention has the amino acid sequence as shown in SEQ ID NO:2, wherein the mutations E233P/L234V/L235A/236del/S239D/A330L/I332E/N434A have been introduced. Preferably this antibody further comprises a light chain having the amino acid sequence as shown in SEQ ID NO:1.

In another embodiment, the heavy chain of the antibody of the invention has the amino acid sequence as shown in SEQ ID NO:2, wherein the mutations E233P/L234V/L235A/236del/S239D/A330L/I332E/M252Y/S254T/T256E have been introduced. Preferably this antibody further comprises a light chain having the amino acid sequence as shown in SEQ ID NO:1.

In another embodiment, the heavy chain of the antibody of the invention has the amino acid sequence as shown in SEQ ID NO:2, wherein the mutations E233P/L234V/L235A/236del/K326A/I332E/E333A/N434A have been introduced. Preferably this antibody further comprises a light chain having the amino acid sequence as shown in SEQ ID NO:1.

In another embodiment, the heavy chain of the antibody of the invention has the amino acid sequence as shown in SEQ ID NO:25. Preferably, this antibody further comprises a light chain having the amino acid sequence as shown in SEQ ID NO:23 or SEQ ID NO:24.

In another embodiment, the heavy chain of the antibody of the invention has the amino acid sequence as shown in SEQ ID NO:26. Preferably, this antibody further comprises a light chain having the amino acid sequence as shown in SEQ ID NO:23 or SEQ ID NO:24.

In another embodiment, the heavy chain of the antibody of the invention has the amino acid sequence as shown in SEQ ID NO:27. Preferably, this antibody further comprises a light chain having the amino acid sequence as shown in SEQ ID NO:23 or SEQ ID NO:24.

In a preferred aspect of the invention, the antibody of the invention is a non-fucosylated antibody or an antibody having reduced fucosylation.

The term "antibody having reduced fucosylation", as used herein, refers to an antibody in which less than 90% of the N-glycans of the antibody are fucosylated. Methods to determine the percentage of fucosylation are known in the art. In one embodiment, less than 75%, or less than 50%, or less than 25% of the N-glycans of the antibody are fucosylated. Most preferably, less than 10% of the N-glycans of the antibody are fucosylated. In a particular embodiment, the N-glycans of the antibody of the invention do not contain any fucose.

Preferably, less than 90% of the N-glycans at N297 (EU numbering) of the antibody are fucosylated. In another embodiment, less than 75%, or less than 50%, or less than 25% of the N-glycans at N297 (EU numbering) of the antibody are fucosylated. Most preferably, less than 10% of the N-glycans at N297 (EU numbering) of the antibody are fucosylated.

In another embodiment, the N-glycans at N297 of the antibody do not contain any fucose.

Non-fucosylated antibodies, sometimes also referred to as afucosylated antibodies, can be generated by various methods. For example, the synergistic knockdown of the genes for α1,6-fucosyltransferase (FUT8) and GDP-mannose 4,6-dehydratase (GMD) in CHO cells can be used to produce monoclonal antibody variants that are fully afucosylated and ADCC-enhanced (see, e.g., Imai-Nishiya et al. (2007) BMC Biotechnol. 7, 84). A method using zinc-finger nucleases (ZFNs) cleaving the FUT8 gene in a region encoding the catalytic core of the α1,6-fucosyltransferase and thus disrupting the corresponding enzymatic function in CHO cells can be used to produce monoclonal antibodies completely lacking core fucose (see, e.g., Malphettes et al. (2010) Biotechnol. Bioeng. 106, 774-783).

Antibodies having reduced fucosylation can be prepared by addition of a decoy substrate such as 2-deoxy-2-fluoro-2-fucose to the culture medium (see, e.g., Dekker et al. (2016) Sci Rep 6:36964), resulting in a reduced incorporation of fucose in the IgG-Fc glycans.

In another embodiment, the antibody of the invention has a high sialic acid content. In increase in sialylation can be achieved, e.g. by simultaneous transfection of cytidine monophosphate-sialic acid synthase (CMP-SAS), cytidine monophosphate-sialic acid transporter (CMP-SAT), and a 2,3-sialyltransferases (see, e.g., Son et al. (2011) Glycobiology 21, 1019-1028).

Affinity to FcRn

The affinity at pH 6 to human FcRn of the antibody of the invention is high. The high affinity binding of the antibody to human FcRn at pH 6 is typically characterized by a $K_D$ value of less than 500 nm. Preferably, the $K_D$ value of the high affinity binding at pH 6 is less than 400 nm, or less than 300 nm, or less than 200 nm. For example, the $K_D$ value characterizing the affinity at pH 6 may be in the range from 5 to 500 nM, or 10 to 400 nM, or 25 to 300 nM, or 50 to 200 nM, or 100 to 175 nM.

In a preferred embodiment, the affinity of the antibody of the invention to human FcRn at pH 6 is greater than the affinity of infliximab to human FcRn at pH 6.0.

The affinity of the antibody of the invention to human FcRn is preferably determined by surface plasmon resonance (SPR), for example as described in Example 4 of this application.

The antibody of the present invention typically has a low affinity to human FcRn at pH 7.4. The low affinity is characterized by a $K_D$ value of greater than 1 μM. Preferably, the low affinity to human FcRn at pH 7.4 is characterized by a $K_D$ value of greater than 2 μM, or greater than 5 μM, or greater than 10 μM.

In a particular embodiment, the low affinity at pH 7.4 is so low that a $K_D$ value cannot be determined by SPR.

In a special embodiment, the ratio of (i) a $K_D$ value for binding of the antibody of the invention to human FcRn at pH 7.4 to (ii) a $K_D$ value for binding to human FcRn at pH 6.0, is at least 50. Preferably, this ratio is at least 100, or at least 150, or at least 200.

Functional Properties of the Antibody

The antibody of the invention is efficiently transported across a polarized cell monolayer from the apical side to the basolateral side. Typically, the transport across the polarized cell monolayer is in a greater amount than that of infliximab, wherein the amount of antibody in infliximab refers to the mass/$cm^2$ of the polarized cell monolayer. The amount of antibody transported across the polarized cell monolayer, relative to the amount of infliximab transported across the polarized cell monolayer, is at least 110%, preferably at least 120%, more preferably at least 130%, or at least 140%, or at least 150% (wherein the amount of transported infliximab is set to 100%).

Furthermore, the antibody is specifically transported across the polarized cell monolayer from the apical side to the basolateral side in the presence of an excess of competing immunoglobulins. This is referred to as specific transport herein.

The percentage of the total mass of immunoglobulins transported across the polarized cell monolayer is greater than the percentage of infliximab transported across the polarized cell monolayer from the apical side to the basolateral side in the presence of a 10-fold excess of competing immunoglobulins. The percentage of antibody of the invention transported across the polarized cell monolayer in the presence of a 10-fold excess of unrelated immunoglobulins, relative to the percentage of infliximab transported across the polarized cell monolayer in the presence of a 10-fold excess of unrelated antibodies, is at least 120%, or at least 130%, or at least 140%, or at least 150% (infliximab is set to be 100%).

Preferably, the polarized cell monolayer is a monolayer of polarized T84 cells. The transport assay mimicking process of transcytosis can be carried out as described in Example 5 of this application.

The antibody of the invention binds to CD16a(V), CD16a (F) and CD16b(NA2).

The antibody of the invention typically binds to CD16a (V) with a $K_D$ of less than 1 μM, preferably less than 500 nM, more preferably less than 100 nM.

The antibody of the invention typically binds to CD16a(F) with a $K_D$ of less than 10 μM, preferably less than 1 μM.

The antibody of the invention typically binds to CD16b (NA2) with a $K_D$ of less than 10 μM, preferably less than 1 μM.

The antibody of the invention is further capable of inducing $CD14^+CD206^+$ macrophages. The level of induction is preferably comparable to, equal to, or greater than that of infliximab.

The antibody of the invention is further capable of suppressing T cell proliferation. The degree of suppression of T cell proliferation is preferably comparable to, equal to, or greater than that of infliximab.

Pharmaceutical Compositions and Treatment

Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom an anti-TNFα antibody is administered can be a mammal, such as a non-primate (e.g., cow, pig, horse, cat, dog, rat, etc.) or a primate (e.g., monkey or human). In certain aspects, the human is a pediatric patient. In other aspects, the human is an adult patient.

Compositions comprising an anti-TNFα antibody and, optionally one or more additional therapeutic agents, such as the second therapeutic agents described below, are described herein. The compositions typically are supplied as part of a sterile, pharmaceutical composition that includes a pharmaceutically acceptable carrier. This composition can be in any suitable form (depending upon the desired method of administering it to a patient).

The anti-TNFα antibodies can be administered to a patient by a variety of routes such as orally, transdermally, subcutaneously, intranasally, intravenously, intramuscularly, intrathecally, topically or locally, e.g. mucosally. The most suitable route for administration in any given case will depend on the particular antibody, the subject, and the nature and severity of the disease and the physical condition of the subject. In one embodiment, the anti-TNFα antibody is administered intravenously.

In a particularly preferred embodiment, the antibody of the invention is administered orally. If the administration is via the oral route the antibody is preferably an IgG, most preferably an $IgG_1$.

The anti-TNFα antibody may be present in a pharmaceutical composition at a concentration sufficient to permit intravenous administration at 0.5 mg/kg body weight to 20 mg/kg body weight. In some embodiments, the concentration of antibody suitable for use in the compositions and methods described herein includes, but is not limited to, 0.5 mg/kg, 0.75 mg/kg, 1 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, or a concentration ranging between any of the foregoing values, e.g., 1 mg/kg to 10 mg/kg, 5 mg/kg to 15 mg/kg, or 10 mg/kg to 18 mg/kg.

The effective dose of an anti-TNFα antibody can range from about 0.001 to about 750 mg/kg per single (e.g., bolus) administration, multiple administrations or continuous administration, or to achieve a serum concentration of 0.01-5000 μg/ml per single (e.g., bolus) administration, multiple administrations or continuous administration, or any effective range or value therein depending on the condition being treated, the route of administration and the age, weight and condition of the subject. In case of oral administration, the serum concentration may be very low or even below the detection limit. In certain embodiments, each dose can range from about 0.5 mg to about 50 mg per kilogram of body weight or from about 3 mg to about 30 mg per kilogram body weight. The antibody can be formulated as an aqueous solution.

In a particularly preferred embodiment, the antibody of the invention is administered orally. If the administration is via the oral route the antibody is preferably an IgG, most preferably an $IgG_1$. If the antibody is administered orally, the daily dose of antibody is typically in the range of about 0.01 mg/kg to about 100 mg/kg of body weight, or about 0.05 mg/kg to about 50 mg/kg of body weight, or about 0.1 mg/kg to about 25 mg/kg of body weight, or about 0.15 mg/kg to about 10 mg/kg of body weight, or about 0.16 mg/kg to about 5 mg/kg of body weight, or about 0.2 mg/kg to about 2 mg/kg of body weight, or about 0.2 mg/kg to about 1 mg/kg of body weight, Generally, advantageous doses are doses of 1 to 200 mg per day, preferably 5 to 100 or 10 to 50 mg per day.

Pharmaceutical compositions can be conveniently presented in unit dose forms containing a predetermined amount of an anti-TNFα antibody per dose. Such a unit can contain 0.5 mg to 5 g, for example, but without limitation, 1 mg, 10 mg, 20 mg, 30 mg, 40 mg, 50 mg, 100 mg, 200 mg, 300 mg, 400 mg, 500 mg, 750 mg, 1000 mg, or any range between any two of the foregoing values, for example 10 mg to 1000 mg, 20 mg to 50 mg, or 30 mg to 300 mg. Pharmaceutically acceptable carriers can take a wide variety of forms depending, e.g., on the condition to be treated or route of administration.

Determination of the effective dosage, total number of doses, and length of treatment an anti-TNFα antibody thereof is well within the capabilities of those skilled in the art, and can be determined using a standard dose escalation study.

Therapeutic formulations of the anti-TNFα antibodies suitable in the methods described herein can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), citrate-phosphate buffers, succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

The pharmaceutical composition of the invention may further comprise at least one salt, e.g. sodium chloride. The salt concentration preferably ranges from 100 mM to 200 mM, e.g. about 150 mM.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonifiers sometimes known as "stabilizers" can be added to ensure isotonicity of liquid compositions and include polyhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinositol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), protease inhibitors and co-solvents.

The formulation herein can also contain a second therapeutic agent in addition to an anti-TNFα antibody thereof. Examples of suitable second therapeutic agents are provided below.

The dosing schedule can vary from once a month to daily depending on a number of clinical factors, including the type of disease, severity of disease, and the patient's sensitivity to the anti-TNFα antibody. In specific embodiments, an anti-TNFα antibody thereof is administered daily, twice weekly, three times a week, every other day, every 5 days, once weekly, every 10 days, every two weeks, every three weeks, every four weeks or once a month, or in any range between any two of the foregoing values, for example from every four days to every month, from every 10 days to every two weeks, or from two to three times a week, etc.

The dosage of an anti-TNFα antibody to be administered will vary according to the particular antibody, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of an anti-TNFα antibody thereof will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

Disorders to be Treated

The invention relates to a method of treating or preventing a human TNFα-related disease in a subject, comprising administering to the subject the antibody as defined herein. The term "TNFα-related disorder" or "TNFα-related disease" refers to any disorder, the onset, progression or the persistence of the symptoms or disease states of which requires the participation of TNFα. Exemplary TNFα-related disorders include, but are not limited to, chronic and/or autoimmune states of inflammation in general, immune mediated inflammatory disorders in general, inflammatory CNS disease, inflammatory diseases affecting the eye, joint, skin, mucous membranes, central nervous system, gastrointestinal tract, urinary tract or lung, states of uveitis in general, retinitis, HLA-B27+ uveitis, Behçet's disease, dry eye syndrome, glaucoma, Sjögren syndrome, diabetes mellitus (incl. diabetic neuropathy), insulin resistance, states of arthritis in general, rheumatoid arthritis, osteoarthritis, reactive arthritis and Reiter's syndrome, juvenile arthritis, ankylosing spondylitis, multiple sclerosis, Guillain-Barré syndrome, myasthenia gravis, amyotrophic lateral sclerosis, sarcoidosis, glomerulonephritis, chronic kidney disease, cystitis, psoriasis (incl. psoriatic arthritis), hidradenitis suppurativa, panniculitis, pyoderma gangrenosum, SAPHO syndrome (synovitis, acne, pustulosis, hyperostosis and osteitis), acne, Sweet's sydrome, pemphigus, Crohn's disease (incl. extraintestinal manifestastations), ulcerative colitis, asthma bronchiale, hypersensitivity pneumonitis, general allergies, allergic rhinitis, allergic sinusitis, chronic obstructive pulmonary disease (COPD), lung fibrosis, Wegener's granulomatosis, Kawasaki syndrome, Giant cell arteritis, Churg-Strauss vasculitis, polyarteritis nodosa, burns, graft versus host disease, host versus graft reactions, rejection episodes following organ or bone marrow transplantation, systemic and local states of vasculitis in general, systemic and cutaneous lupus erythematodes, polymyositis and dermatomyositis, sclerodermia, pre-eclampsia, acute and chronic pancreatitis, viral hepatitis, alcoholic hepatitis, postsurgical inflammation such as after eye surgery (e.g. cataract (eye lens replacement) or glaucoma surgery), joint surgery (incl. arthroscopic surgery), surgery at joint-related structures (e.g. ligaments), oral and/or dental surgery, minimally invasive cardiovascular procedures (e.g. PTCA, atherectomy, stent placement), laparoscopic and/or endoscopic intra-abdominal and gynecological procedures, endoscopic urological procedures (e.g. prostate surgery, ureteroscopy, cystoscopy, interstitial cystitis), or perioperative inflammation (prevention) in general, bullous dermatitis, neutrophilic dermatitis, toxic epidermal necrolysis, pustular dermatitis, cerebral malaria, hemolytic uremic syndrome, allograft rejection, otitis media, snakebite, erythema nodosum, myelodysplastic syndromes, primary sclerosing cholangitis, seronegative spondylartheropathy, autoimmune hematolytic anemia, orofacial granulamatosis, pyostomatitis vegetans, aphthous stomatitis, geographic tongue, migratory stomatitis, Alzheimer disease, Parkinson's disease, Huntington's disease, Bell's palsy, Creutzfeld-Jakob disease and neuro-degenerative conditions in general.

Cancer-related osteolysis, cancer-related inflammation, cancer-related pain, cancer-related cachexia, bone metastases, acute and chronic forms of pain, irrespective whether these are caused by central or peripheral effects of TNFα and whether they are classified as inflammatory, nociceptive or neuropathic forms of pain, sciatica, low back pain, carpal tunnel syndrome, complex regional pain syndrome (CRPS), gout, postherpetic neuralgia, fibromyalgia, local pain states, chronic pain syndroms due to metastatic tumor, dismenorrhea.

Particular disorders to be treated include states of arthritis in general, rheumatoid arthritis, osteoarthritis, reactive arthritis, juvenile arthritis; psoriasis incl. psoriatic arthritis; inflammatory bowel disease, including Crohn's disease, ulcerative colitis incl. proctitis, sigmoiditis, proctosigmoiditis, left-sided colitis, extensive colitis and pancolitis, undetermined colitis, microscopic colitis incl. collagenous and lymphocytic colitis, colitis in connective tissue disease, diversion colitis, colitis in diverticular disease, eosinophilic colitis and pouchitis.

Most preferably, the antibody of the invention is used to treat an inflammatory bowel disease, in particular Crohn's disease, ulcerative colitis or microscopic colitis. The Crohn's disease may be ileal, colonic, ileocolonic or isolated upper Crohn's disease (gastric, duodenal and/or jejunal) including non-stricturing/non-penetrating, stricturing, penetrating and perianal disease behavior, allowing any combination of localization and disease behavior of any of the above mentioned. The ulcerative colitis may be ulcerative proctitis, proctosigmoiditis, left-sided colitis, pan-ulcerative colitis and pouchitis.

Combination Therapy and Other Aspects

Preferably, the patient being treated with an anti-TNFα antibody thereof is also treated with another conventional medicament. For example, a patient suffering from inflammatory bowel disease, especially if having moderate to severe disease is typically also being treated with mesalazine or derivatives or prodrugs thereof, corticosteroids, e.g. budesonide or prednisolone (oral or i.v.), immunosuppressants, e.g. azathioprine/6-mercaptopurine (6-MP) or methotrexate, cyclosporine or tacrolimus. Other medicaments which can be co-administered to the patient include other anti-TNFα antibodies (e.g. infliximab, adalimumab, etanercept, certolizumab pegol, golimumab), integrin antagonists (e.g. natalizumab, vedolizumab), anti-IL-23 antibodies (e.g. MED12070), anti-β7 antibodies (e.g. etrolizumab), JAK inhibitors in the JAK/STAT pathway (e.g. tofacitinib), and others. Further medicaments which can be co-administered to the patient include immunosupressants (e.g. azathioprine/6-MP or methotrexate or oral cyclosporine) in order to maintain stable and longer remission. Yet another aspect of the invention is the use of an anti-TNFα antibody as defined hereinabove for reducing inflammation.

Yet another aspect of the invention is an anti-TNFα antibody as defined hereinabove for use in reducing inflammation in a patient suffering from an inflammatory condition.

A further aspect of this invention is a method of treating an inflammatory condition, comprising administering to a patient in need thereof an effective amount of an anti-TNFα antibody as defined hereinabove. The inflammatory condition is preferably one of the conditions described above.

A further aspect of this invention is a method of preventing an inflammatory condition, comprising administering to a patient in need thereof an effective amount of an anti-TNFα antibody as defined hereinabove. The inflammatory condition is preferably one of the conditions described above.

Yet another aspect of the present invention is a method for improving the transcytosis of an antibody directed against TNFα, comprising introducing the substitutions E233P, L234V and L235A, deleting G236 and introducing the following further substitution(s) (a) or (b):

(a) M252Y, S254T and T256E (b) N434A;

and optionally further introducing one or more of the other substitutions described herein; so as to obtain a modified antibody having improved transcytosis. The modified antibody is preferably an antibody as described hereinabove.

Yet another aspect of the present invention is a method for extending the plasma half-life of an antibody directed against TNFα, comprising introducing the substitutions E233P, L234V and L235A, deleting G236 and introducing the following further substitution(s) (a) or (b):

(a) M252Y, S254T and T256E (b) N434A;

and optionally further introducing one or more of the other substitutions described herein; so as to obtain a modified antibody having an extended plasma half-life. The modified antibody is preferably an antibody as described hereinabove. The plasma half-life may be increased by at least 10%, or least 20%, or least 30%, or least 40%, or least 50%, relative to the plasma half-life of the non-modified antibody (i.e., the respective parent antibody lacking the recited mutations).

Yet another aspect of the present invention is a method of improving the resistance against proteolytic degradation of an antibody directed against TNFα, comprising introducing the substitutions E233P, L234V and L235A, deleting G236 and introducing the following further substitution(s) (a) or (b):

(a) M252Y, S254T and T256E (b) N434A;

and optionally further introducing one or more of the other substitutions described herein; so as to obtain a modified antibody having improved resistance to proteolytic degradation. The modified antibody is preferably an antibody as described hereinabove.

TABLE 1

Overview of the sequences of the sequence listing.

| SEQ ID NO: | Description of the amino acid sequence |
|---|---|
| 1 | Light chain of Ab-wt, the parent antibody of the modified antibodies used in the examples |
| 2 | Heavy chain of Ab-wt, the parent of the modified antibodies used in the examples |
| 3 | CDR L1 of clone 16-22-H05 |
| 4 | CDR L2 of clone 16-22-H05 |
| 5 | CDR L3 of clone 16-22-H05 |
| 6 | CDR H1 of clone 16-22-H05 |
| 7 | CDR H2 of clone 16-22-H05 |
| 8 | CDR H3 of clone 16-22-H05 |
| 9 | $V_H$ of humanized IgG of clone 16-22-H05 |
| 10 | $V_L$ of humanized IgG of clone 16-22-H05 |
| 11 | Heavy chain of Ab-YTE-DLE-PVAΔG (based on clone 16-22-H05) |
| 12 | Heavy chain of Ab-A-DLE-PVAΔG (based on clone 16-22-H05) |
| 13 | Heavy chain of Ab-A-AEA-PVAΔG (based on clone 16-22-H05) |
| 14 | CDR L1 of clone 17-22-B03 |
| 15 | CDR L2 of clone 17-22-B03 |
| 16 | CDR L3 of clone 17-22-B03 |
| 17 | CDR H1 of clone 17-22-B03 |
| 18 | CDR H2 of clone 17-22-B03 |
| 19 | CDR H3 of clone 17-22-B03 |
| 20 | $V_H$ of humanized IgG of clone 17-22-B03 |
| 21 | $V_L$ of humanized IgG of clone 17-22-B03 (sc08) |
| 22 | $V_L$ of humanized IgG of clone 17-22-B03 (sc02) |
| 23 | Light chain of humanized IgG of clone 17-22-B03 (sc08) |
| 24 | Light chain of humanized IgG of clone 17-22-B03 (sc02) |
| 25 | Heavy chain of Ab-YTE-DLE-PVAΔG (based on clone 17-22-B03) |
| 26 | Heavy chain of Ab-A-DLE-PVAΔG (based on clone 17-22-B03) |
| 27 | Heavy chain of Ab-A-AEA-PVAΔG (based on clone 17-22-B03) |
| 28 | Fc region including hinge region of Ab-YTE-DLE-PVAΔG |
| 29 | Fc region including hinge region of Ab-A-DLE-PVAΔG |
| 30 | Fc region including hinge region of Ab-A-AEA-PVAΔG |

EXAMPLES

Antibody Variants

Figure 10:
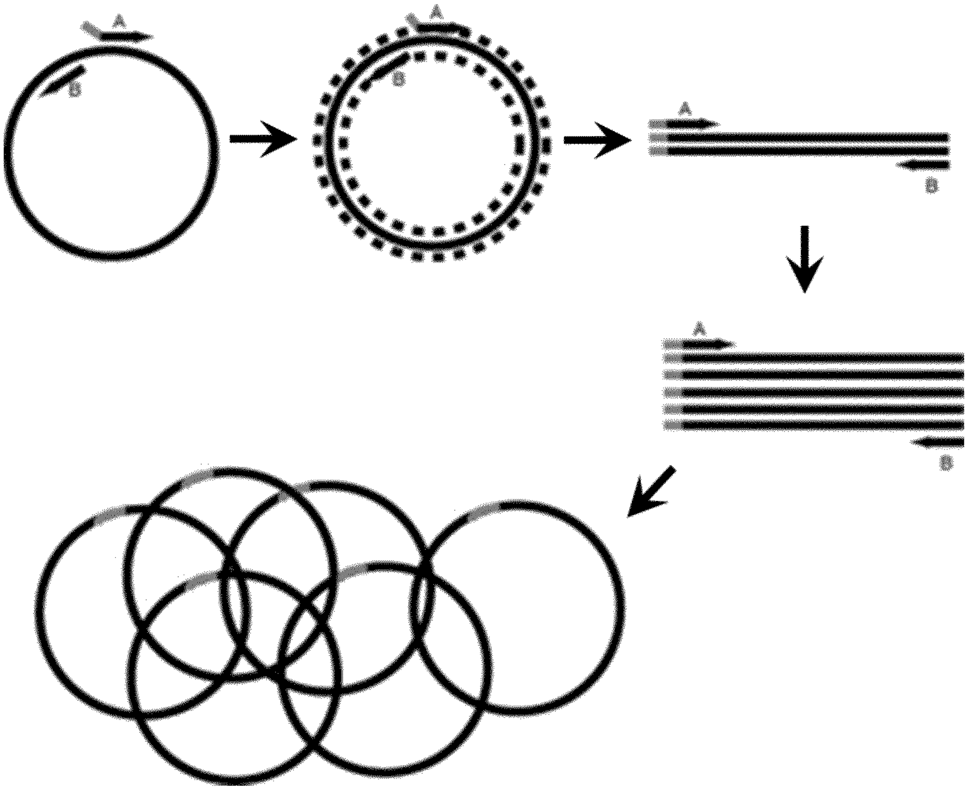
FIG. 10: Schematic presentation of site directed mutagenesis.

Several variants of an anti-TNFα antibody (hereinafter referred to as "parent antibody" or "Ab-wt") were generated by introducing substitutions in the Fc region of the antibody amino acid sequence. The light chain of Ab-wt has the amino acid sequence as shown in SEQ ID NO:1, and the heavy chain of Ab-wt has the amino acid sequence as shown in SEQ ID NO:2. The mutations were introduced by site-directed mutagenesis by established methods. Briefly, mutations were introduced by PCR. The forward primer was designed to contain the intended mutation while the reverse primer was designed so that the 5' ends of the two primers anneal back-to-back (but do not overlap) (FIG. 10). PCR was run for 25 cycles (98° C. for 10 s, 64° C. for 30 s, 72° C. for 3 min). Before running the PCR product on an agarose gel, the non-mutated PCR template was removed from the pool of PCR products using the restriction enzyme DpnI. Following gel purification of the PCR product the blunt ends were ligated to obtain a circularized plasmid which was transformed into competent *E. coli* cells. Following overnight incubation several colonies were picked, the plasmid DNA isolated and sequenced to confirm that the mutation had been incorporated.

TABLE 2

Generated antibody variants of an anti-TNFα antibody (EU numbering)

| Designation | Mutations relative to parent antibody |
|---|---|
| Ab-wt* | None (= parent antibody) |
| Ab-YTE-DLE-PVAΔG** | M252Y/S254T/T256E-S239D/A330L/I332E-E233P/L234V/L235A/G236del |
| Ab-A-DLE-PVAΔG** | N434A-S239D/A330L/I332E-E233P/L234V/L235A/G236del |
| Ab-A-AEA-PVAΔG** | N434A-K326A/I332E/E333A-E233P/L234V/L235A/G236del |

*antibody not according to the invention;
**antibody according to the invention

Example 1. Affinity to TNFα

Method:

Affinity to TNFα was measured by Biacore. A CM5 chip was prepared using standard amine immobilisation Biacore procedures. Upon insertion of a CM5 chip the system was primed and then normalised with BIA-normalising solution (Biacore Preventative Maintenance Kit 2). The chip was added to the system with Phosphate Buffered Saline Tween-20 (PBS-T) running buffer; prior to immobilisation the chip surface was primed with three injections of 50 mM NaOH. Protein A was immobilised on the chip surface. For this, the protein was diluted to 5 μg/mL into 10 mM acetate buffer at pH 4.5 and injected so to generate a bound response of ~1000 RU's in all 4 flow cells. To remove non-covalently bound material from all the chip flow cells, three 15 second 50 mM NaOH washes were performed. On the Protein A chip, antibody was captured in flow cells 2 and 4, with flow cells 1 and 3 used for reference subtraction. The trial antibodies were diluted in PBS-T to 10 nM and 2.5-7.5 uL injected to obtain 120 RU of captured antibody. The analyte TNFα was prepared at 500 μg/mL in water as directed by the supplier and further diluted into the running buffer PBS-T. Single cycle kinetics was used to estimate the steady state affinity. For each single cycle analysis cycle a titration of 5 analyte concentrations were injected over the ligand and then the dissociation of the complex was measured. The surface was regenerated using glycine pH 1.7. A double referencing method was employed in which data from the ligand bound capture surface (fc 2 and 4) were subtracted from the references surfaces where no ligand was captured (fc 1 and 3 respectively). Blank injections of buffer were run every 3-4 cycles and then subtracted from analyte injection cycles, to correct for small changes in the ligand capture surface. Repeat injections of analyte at the start and end of each analytical run were used to check for sample degradation, or changes in the instrument performance. All analysis was performed at 25° C. and the sample rack was incubated at 10° C. during experimental runs. Each experiment was run at least three times. A 1-to-1 binding model was used to fit the resulting kinetic data.

Results:

All antibodies displayed similar binding kinetics to TNFα indicating that any introduced modification had not led to significant changes in the antigen binding region.

TABLE 3

Binding kinetics of human IgG1 variants to TNFα as determined by SPR

| | $k_a$ ($10^6$/Ms) | $k_d$ ($10^{-5}$/s) | $K_D$ (pM) |
|---|---|---|---|
| Ab-wt | 8.37 ± 0.11 | 3.45 ± 0.20 | 4.13 ± 0.19 |
| Ab-YTE-DLE-PVAΔG | 8.14 ± 0.37 | 1.28 ± 0.31 | 1.57 ± 0.31 |
| Ab-A-DLE-PVAΔG | 11.3 ± 3.58 | 3.04 ± 0.14 | 2.88 ± 0.87 |
| Ab-A-AEA-PVAΔG | 9.16 ± 3.24 | 2.19 ± 0.53 | 2.51 ± 0.75 |

Example 2. Potency

Method:

L929 cells were incubated with 0.25 ng/mL of TNFα and 1 μg/well of actinomycin D in the presence of serial dilutions of anti-TNFα antibody variants. Following incubation for 20 h at 37° C./5% $CO_2$, the proliferative responses were measured using MTS (3-(4,5-dimethylthiazol-2-yl)-5-(3-carboxymethoxyphenyl)-2-(4-sulfophenyl)-2H-tetrazolium and an electron coupling reagent (phenazine ethosulfate, PES). MTS was converted into formazan product by dehydrogenase enzymes present in metabolically active cells. The quantity of formazan product as measured by absorbance at 492 nm was directly proportional to the number of living cells in culture.

Results:

The results are shown in FIG. 1. The introduction of mutations into the Fc region of the anti-TNFα antibody did not affect the potency.

Example 3. Affinity to Fcγ Receptors (CD16a, CD16b)

Method:

Affinity to FcγRs was measured by Biacore. A CM5 chip was prepared using standard amine immobilisation Biacore procedures. Upon insertion of a CM5 chip the system was primed and then normalised with BIA-normalizing solution (Biacore Preventative Maintenance Kit 2). The chip was added to the system with PBS-T running buffer; prior to immobilisation the chip surface was primed with three injections of 50 mM NaOH. FcγRs were immobilised on the chip surface using a His-tag capture system. The anti-His tag chip was prepared according to the Biacore kit instructions, with ~12000 RU's of the antibody deposited on all 4 flow cells. To remove non-covalently bound material from all the chip flow cells, three 30 second 10 mM glycine pH 1.5 washes were performed. The Fcγ receptors were diluted in PBS-T to a range of 0.5-2 μg/mL, with 2.5-5.0 μL injected onto the chip generating capture levels between 60 and 200 RU's. Antibodies were diluted into PBS-T prior to analysis. Single cycle kinetics were used to estimate the steady state affinity. For each single cycle analysis cycle a titration of 5 antibody concentrations were injected over the FcγR ligand and then the dissociation of the complex was measured. The surface was regenerated using the recommended solution, 10 mM glycine pH 1.5 for the anti-His capture surface. A double referencing method was employed in which data from the ligand bound capture surface (fc 2 and 4) were subtracted from the references surfaces where no ligand was captured (fc 1 and 3 respectively). Blank injections of buffer were run for every antibody titration cycle and then subtracted from analyte injection cycles, to correct for small changes in the ligand capture surface. All analysis was performed at 25° C. and the sample rack was incubated at 10° C. during experimental runs. Each experiment was run at least three times.

Results:

The introduction of the mutations did not affect the affinity to CD16a(V), CD16a(F) and CD16b. However, some antibody variants exhibited increased binding to CD16a. Especially Ab-A-DLE-PVAΔG had an improved binding to the low affinity CD16a receptor and to CD16b.

TABLE 4

Affinity to Fcγ receptors CD16a(V), CD16a(F) and CD16b as determined by SPR. The mean and standard deviation affinity calculated from two or more independent experiments is shown.

| | Affinity ($K_D$) | | |
|---|---|---|---|
| | CD16a(V) (nM) | CD16a(F) (μM) | CD16b(NA2) (μM) |
| Ab-wt | 184 ± 31.9 | nd | >3.00 |
| Ab-YTE-DLE-PVAΔG | 117 ± 13.9 | nd | 1.03 ± 0.54 |
| Ab-A-DLE-PVAΔG | 68.7 ± 14.1 | 0.11 ± 0.02 | 0.47 ± 0.10 |
| Ab-A-AEA-PVAΔG | 260 ± 9.73 | nd | 5.18 ± 0.08 |

Example 4. Affinity to FcRn

Method:

SPR was performed using a Biacore 3000 instrument with CM5 sensor chips coupled with anti-TNFα IgG1 antibodies (~500 resonance units (RU)) using amine-coupling chemistry as described by the manufacturer. The coupling was performed by injecting 2.0 ug/mL of each protein in 10 mM sodium acetate, pH 4.5, using the amine-coupling kit (GE Healthcare). HBS-P buffer pH 7.4 (10 mM HEPES, 150 mM NaCl, 0.005% surfactant P20) or phosphate buffer pH 6.0 (67 nM phosphate buffer, 150 mM NaCl, 0.005% Tween 20) were used as running and dilution buffer. Binding kinetics were determined by injecting titrated amounts (1000—31.2 nM) of monomeric His-tagged human FcRn (hFcRn) over immobilised antibodies at pH 7.4 or pH 6.0. All SPR experiments were conducted at 25° C. with a flow rate of 40 ul/min. Binding data were zero-adjusted, and reference cell value subtracted. The Langmuir 1:1 ligand binding model provided by the BIAevaluation software (version 4.1) was used to determine the binding kinetics.

Results:

The results showed that the wild-type antibody Ab-wt bound strictly pH dependently to hFcRn. All engineered antibody variants have a higher affinity to FcRn at pH 6.0, but kept their pH dependency and did not bind to the receptor at pH 7.4. All antibody variants showed improved binding to FcRn compared to infliximab which contains a wildtype IgG1 Fc region.

TABLE 5

Affinity of anti-TNFα antibody variants to FcRn at pH 6.0 and pH 7.4 as determined by SPR

| | pH 6.0 | | | pH 7.4 |
|---|---|---|---|---|
| | $K_D$ (nM) | Fold change from wt | Fold change from IFX | $K_D$ (nM) |
| Ab-wt | 1000 | | | NA |
| Ab-YTE-DLE-PVAΔG | 90.0 | 11.1 | 4.7 | NA |
| Ab-A-DLE-PVAΔG | 157 | 6.4 | 2.7 | NA |
| IFX | 425 | | | NA |

NA: not acquired due to weak binding.

Example 5. Transcytosis

Method:

Transwell filters (1.12 $cm^2$) with collagen coated polytetrafluoroethylene (PTFE) membranes with 0.4 μm pore size were incubated 0/N in complete growth medium followed by seeding of $1.0\times10^6$ T84 cells per well. Transepithelial electrical resistance (TEER) was monitored daily using a MILLICELL-ERS-2 volt-ohm meter. The cultures were grown for 4-5 days before reaching confluence with a TEER value of ~1000-1300 $\Omega\times cm^2$. Prior to experiments the monolayers were starved for 1 h in Hank's Balanced Salt Solution (HBSS). Then, 400 nM of the antibody variants or IFX alone or together with 4000 nM human myeloma IgG with irrelevant specificity were added to the apical Transwell chamber. Samples were collected from the basolateral reservoir at 0 and 4 h post adding. Antibody concentrations in the basolateral reservoir were determined by ELISA. Briefly, 96-well Maxisorp plates were coated 0/N with either recombinant TNFα or an anti-human Fc specific antibody from goat, both diluted to 1 μg/ml in PBS. Subsequently, the plates were blocked with PBS containing 4% skimmed milk for 2 h at RT followed by washing 4 times with PBS containing 0.05% Tween 20. Samples collected during the transcytosis experiments were added to the wells and incubated for 2 h at RT before washing as above. Captured antibody variants, IFX or total IgG were detected using an alkaline phosphatase (ALP)-conjugated anti-human Fc specific antibody from goat. Binding was visualized by addition of 100 μl ALP-substrate and the 405 nm absorption spectrum was recorded. The amount of antibody variants, IFX and total IgG transported were calculated from standard curves of each of the individual antibody variants.

Transcytosis of Antibody Variants Across Polarized Human Epithelial Cells

Figure 2:
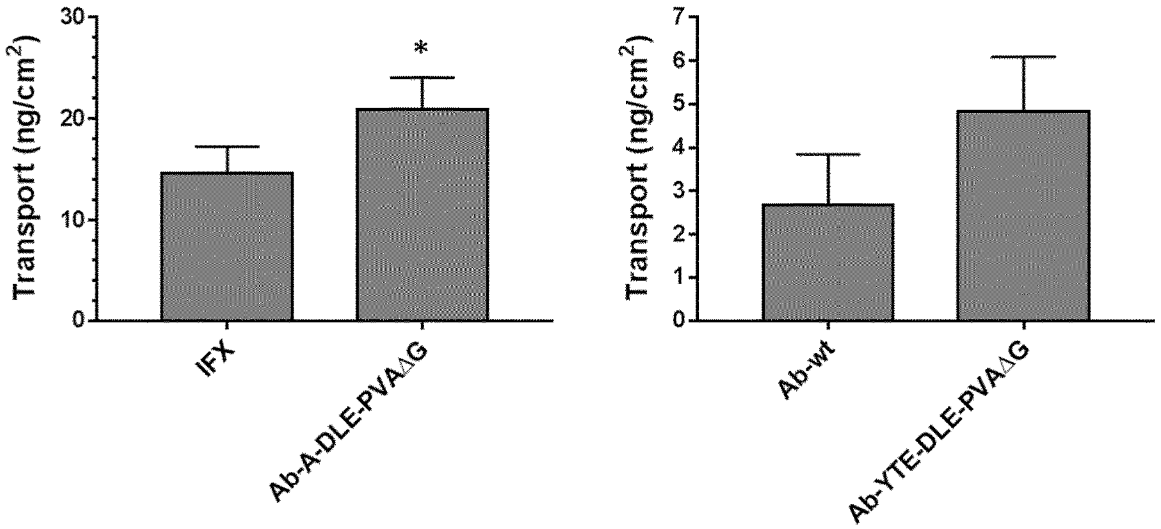
FIG. 2: Transport of anti-TNFα IgG variants across polarized T84 cells. The amounts of anti-TNFα antibody variants and Infliximab (IFX) from the apical to the basolateral reservoir at 4 hours post adding. Presented as ng/$cm^2$. Error bars indicate SD of two to four individual monolayers.

Results:

The engineered anti-TNFα antibody variants were tested for transcytosis across a cell monolayer and compared to the wt antibody or IFX as another human IgG1 anti-TNFα antibody. The results are depicted in FIG. 2. The wt anti-TNFα antibody was transported from the apical to the basolateral reservoir. Of the antibody panel of the engineered variants for improved binding to FcRn, somewhat more of Ab-YTE-DLE-PVΔG was shown to be released at the basolateral side compared to Ab-wt. Compared to IFX, another IgG1 antibody with a wt Fc region, Ab-A-DLE-PVΔG was transported about 1.8-fold more efficiently.

Figure 3:
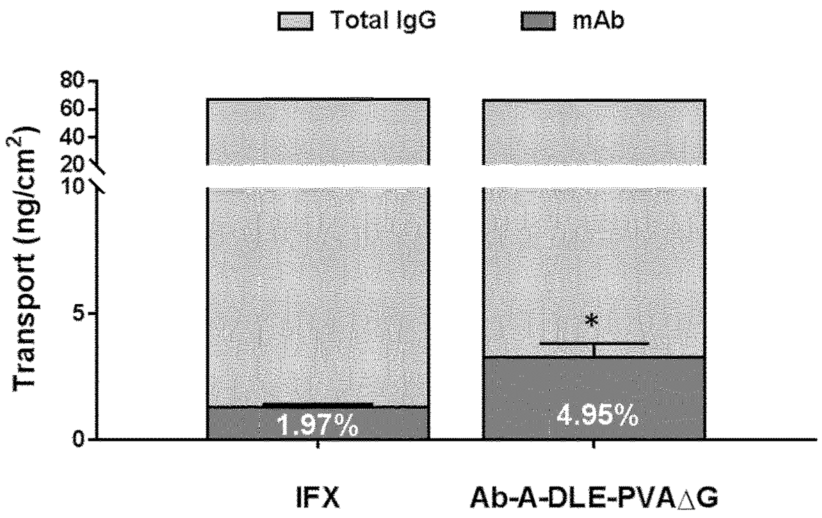
FIG. 3: Transport of anti-TNFα IgG variants across polarized T84 cells in the presence of excess amounts of myeloma IgG. The amounts of the anti-TNFα IFX and Ab variants transported from the apical to the basolateral reservoir in the presence of 10-fold excess of human myeloma IgG at 4 hours post adding. Presented as ng/$cm^2$. Error bars indicate SD of three to four individual monolayers.

Transcytosis of Antibody Variants Across Polarized Human Epithelial Cells in the Presence of Competing IgG Results:

The total amount of immunoglobulin transported across a polarized T84 cell monolayer from the apical to the basolateral reservoir when the anti-TNFα antibody variants were incubated with a 10-fold excess of human myeloma IgG at 4 hours post adding was comparable for all antibodies. However, an increased affinity to FcRn at pH 6.0 resulted in a significantly higher percentage of specific anti-TNFα transport across the cell monolayer also in the presence of an excess of competing human IgG with irrelevant specificity. The results are depicted in FIG. 3.

Example 6. ADCC

Method:

An ADCC reporter bioassay core kit from Promega was used. Briefly, mTNFα CHO-K1 target cells at $1\times10^5$/mL were seeded on white (clear bottom) tissue culture plates, 100 μL per well. The plates were incubated 0/N at 37° C./5% $CO_2$. On day 2, 95 μL of assay medium was removed and replaced with 25 μL of engineered Jurkat effector cells at $3\times10^6$/mL. The plates were then incubated for 6 h at 37° C./5% $CO_2$. The BioGlo™ reagent was prepared towards the end of the incubation. Plates were equilibrated to RT for 10-20 min before adding 75 μL of BioGlo™ reagent per well. After 5-10 min of incubation in the dark, luminescence was measured. A 4-PL model was used to fit the data.

Figure 4:
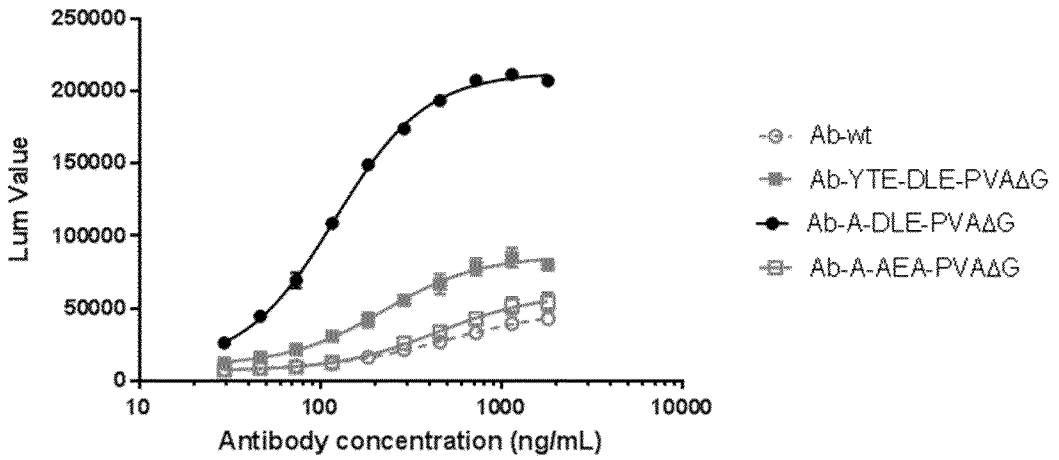
FIG. 4: ADCC activity. Induction of ADCC by anti-TNFα antibody variants and Ab-wt.

Results:

The results (see FIG. 4) showed that all of the anti-TNFα antibodies induced ADCC but with distinct strengths. Compared to the wildtype antibody Ab-wt, Ab-A-AEA-PVΔG showed similar ADCC activity, while the other antibody variants showed increased ADCC. Specifically Ab-A-DLE-PVΔG had significantly improved ADCC.

Example 7. Induction of Regulatory Macrophages

Method:

Peripheral blood mononuclear cells (PBMC) were isolated from buffy coats of healthy donors. Cells were isolated through Ficoll gradient centrifugation. Cells of two individual donors were mixed in equal numbers and $2\times10^5$ cells of the mixture were plated in 96 well plates in a total volume of 100 μL/well. Cells were incubated for 48 h at 37° C./5% $CO_2$. After 48 h, anti-TNFα antibody variants or IFX were added to reach a final concentration of 10 μg/mL. Each compound was added in replicates of five or six. Final volume was 150 μL/well. Human serum IgG1 (Sigma #15154) was used as control. After addition of the compounds, mixed lymphocyte reactions (MLRs) were cultured for another 4 days at 37° C./5% $CO_2$. Afterwards, plates were washed using PBS/5 mM EDTA (PBS/EDTA) and incubated with 50 μL/well PBS/EDTA for 20 min at RT. Plates were centrifuged and liquid was flicked out. Antibody was diluted in PBS/EDTA (anti-CD14-PE, anti-CD206-APC, both diluted 1:10). Cells were resuspended in 50 μL of antibody solution and incubated for 20 min at RT. Afterwards, cells were washed with PBS/EDTA and resuspended in 50 μL PBS/EDTA. Stained samples were analysed on a FACS Fortessa using FACSDiva software. Analysis was performed using FlowJo software.

Figure 5:
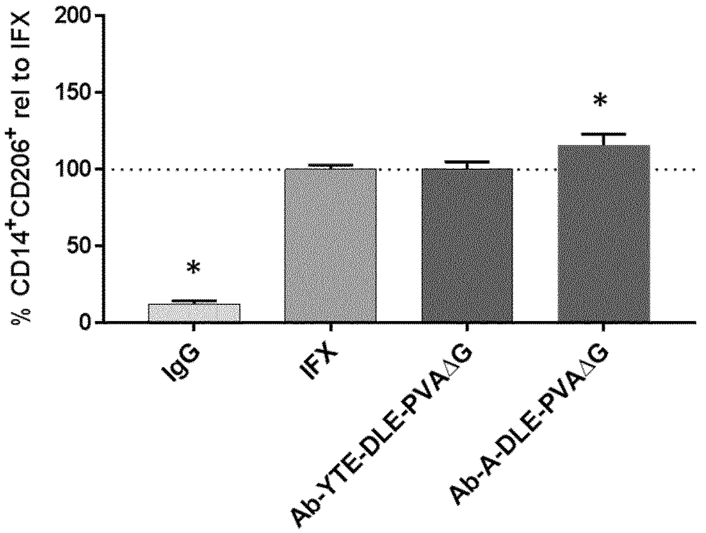
FIG. 5: Induction of $CD14^+CD206^+$ macrophages by each compound relative to the induction of IFX. Summarized data of 4 independent experiments. Bars represent mean, error bars represent SEM.

Results:

Induction of regulatory macrophages was analysed in four independent MLRs and was successful in all experiments (comparing IFX to IgG control). The results are shown in FIG. 5. The levels of induction by IFX can differ between experiments due to the fact that each experiment was performed using different donors with inter-individual variation. All tested anti-TNFα antibody variants induced $CD14^+$ $CD206^+$ regulatory macrophages with slight variation between the compounds. Ab-A-DLE-PVΔG induced more regulatory macrophages than IFX.

Example 8. Inhibition of T-Cell Proliferation

Method:

PBMC were isolated from buffy coats of healthy donors. Cells were isolated through Ficoll gradient centrifugation. Cells of two individual donors were mixed in equal numbers and $2\times10^5$ cells of the mixture were plated in 96 well plates in a total volume of 100 μL/well. Cells were incubated for 48 h at 37° C./5% $CO_2$. After 48 h, anti-TNFα antibody variants or IFX were added to reach a final concentration of 10 μg/mL. Each compound was added in replicates of five or six. Final volume was 150 μL/well. Human serum IgG1 (Sigma #15154) was used as control. After addition of the compounds, mixed lymphocyte reactions (MLRs) were cultured for another 2 days at 37° C./5% $CO_2$. Afterwards, tritiated thymidine ($^3H$ thymidine, 0.5 microCurie/well) was added to the cultures. Cultures were further incubated for 18 h at 37° C./5% $CO_2$. Samples were harvested using a Microbeta Filtermat 96 cell harvester and analysed using a Microbeta MicroplateCounter equipped with a single detector. Samples were counted for 10 seconds/well and converted to counts per minute (cpm).

Figure 6:
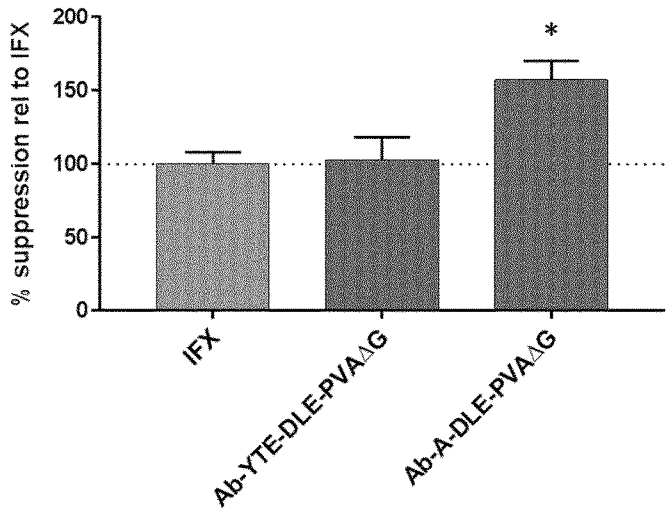
FIG. 6: Suppression of T-cell proliferation by each compound relative to IFX. Summarized data of 3 independent experiments. Bars represent mean, error bars represent SEM.

Results:

Inhibition of T-cell proliferation was measured in three independent MLRs and was defined as successful if IFX as positive control induced suppression. The levels of suppression by IFX in individual experiments can differ presumably due to the variance in regulatory macrophage induction. In each experiment, the potential of the anti-TNFα antibody variants to suppress T-cell proliferation was calculated relative to the positive control IFX. Antibody Ab-A-DLE-PVΔG showed significantly enhanced suppression compared to IFX while suppression by Ab-YTE-DLE-PVΔG was comparable to IFX (see FIG. 6).

Example 9. Protease Stability

Methods:

Analysis was performed under reducing and non-reducing conditions. The corresponding sample buffer from the PerkinElmer Protein Express Reagent Kit with and without the reducing agent DTT was used to quench the reaction (i.e. as stopping reagents).

To be able to differentiate between the variants, the amount of protease per IgG was chosen as follows that degradation-time profiles could be obtained in between 30 hours. Analysis was performed using the microchip based electrophoresis system.

IdeS Digestion

To prepare the working solution (ws), one IdeS aliquot was reconstituted in 100 μL Milli-Q water. IdeS ws and samples were combined in a 1:1 (v/v) ratio and homogenized thoroughly. The solution was incubated at 37° C., samples were pulled after 5, 10, 30, 60 minutes and quenched with one of the stopping reagents. Molar ratio of protease/IgG: 4:1.

GluC Digestion

To prepare the working solution (ws), the GluC stock was diluted with 2× GluC reaction buffer to a concentration of 50 μg/mL. GluC ws and samples were combined in a 1:1 (v/v) ratio and homogenized thoroughly. The solution was incubated at 37° C., samples were pulled after 2, 6, 24, 30 hours and quenched with one of the stopping reagents. Molar ratio of IgG/protease: 4:1.

MMP-3 Digestion

The chymotrypsin stock was diluted with assay buffer MMP to 50 μg/mL. MMP-3 á 0.186 mg/mL was spiked with the diluted chymotrypsin in a 1:1 (v/v) ratio and incubated at 37° C. for 30 minutes. Activation was stopped with PMSF in a final concentration of 2 mM. To prepare the working solution (ws), activated MMP-3 was diluted in assay buffer MMP to 3.72 μg/mL.

MMP-3 ws and samples were combined in a 1:1 (v/v) ratio and homogenized thoroughly. The solution was incubated at 37° C., samples were pulled after 2, 6, 24, 30 hours and quenched with one of the stopping reagents. Molar ratio of IgG/protease: 98:1.

Figure 7:
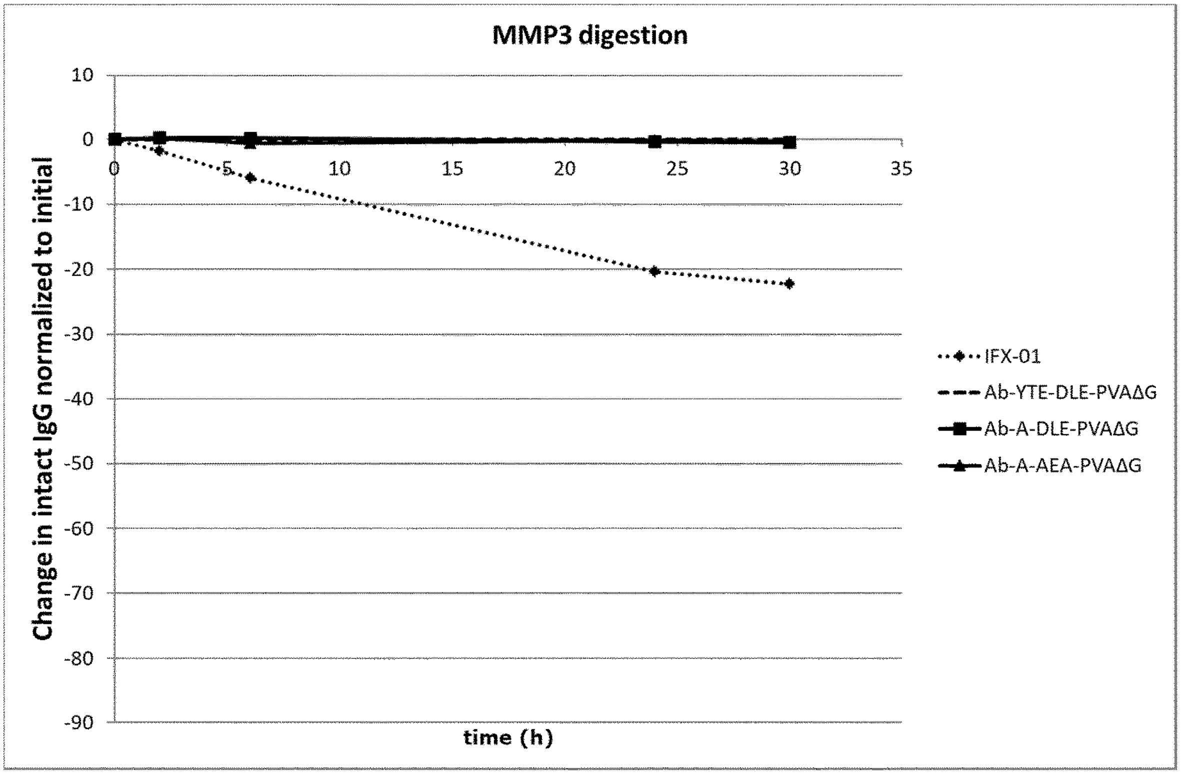
FIG. 7: Resistance to proteolytic degradation by MMP-3.
Figure 8:
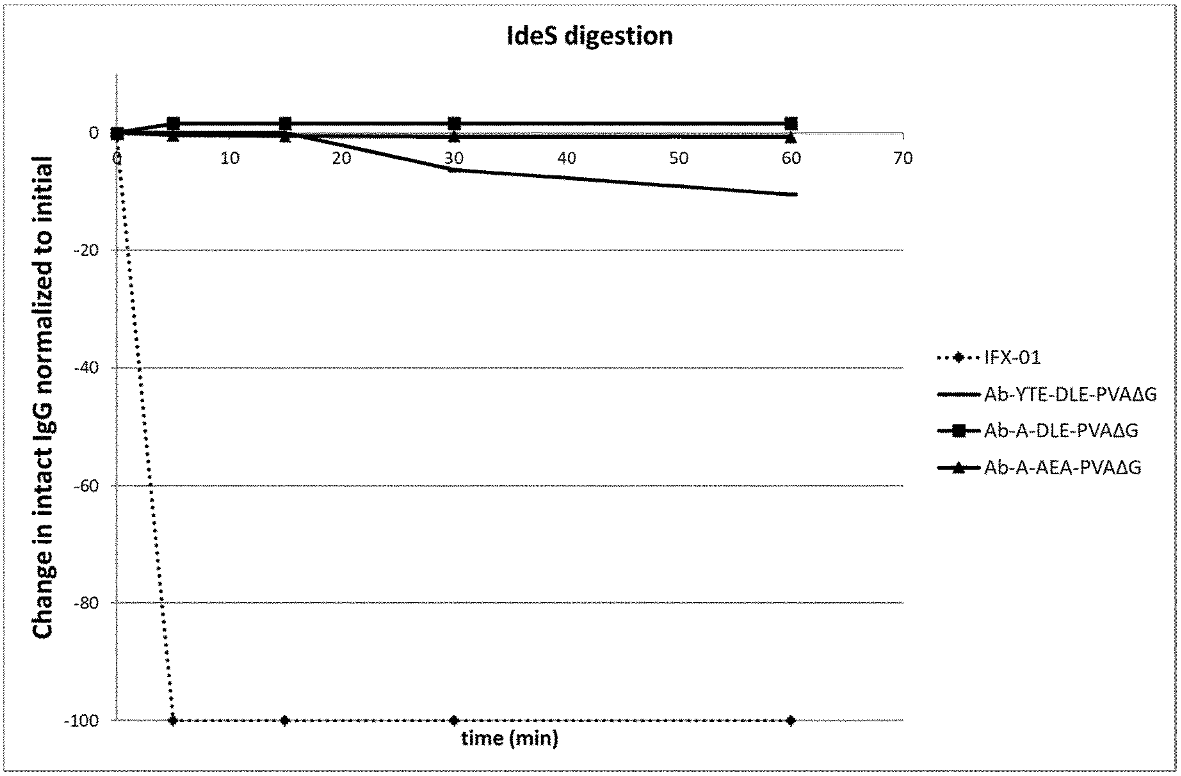
FIG. 8: Resistance to proteolytic degradation by IdeS.
Figure 9:
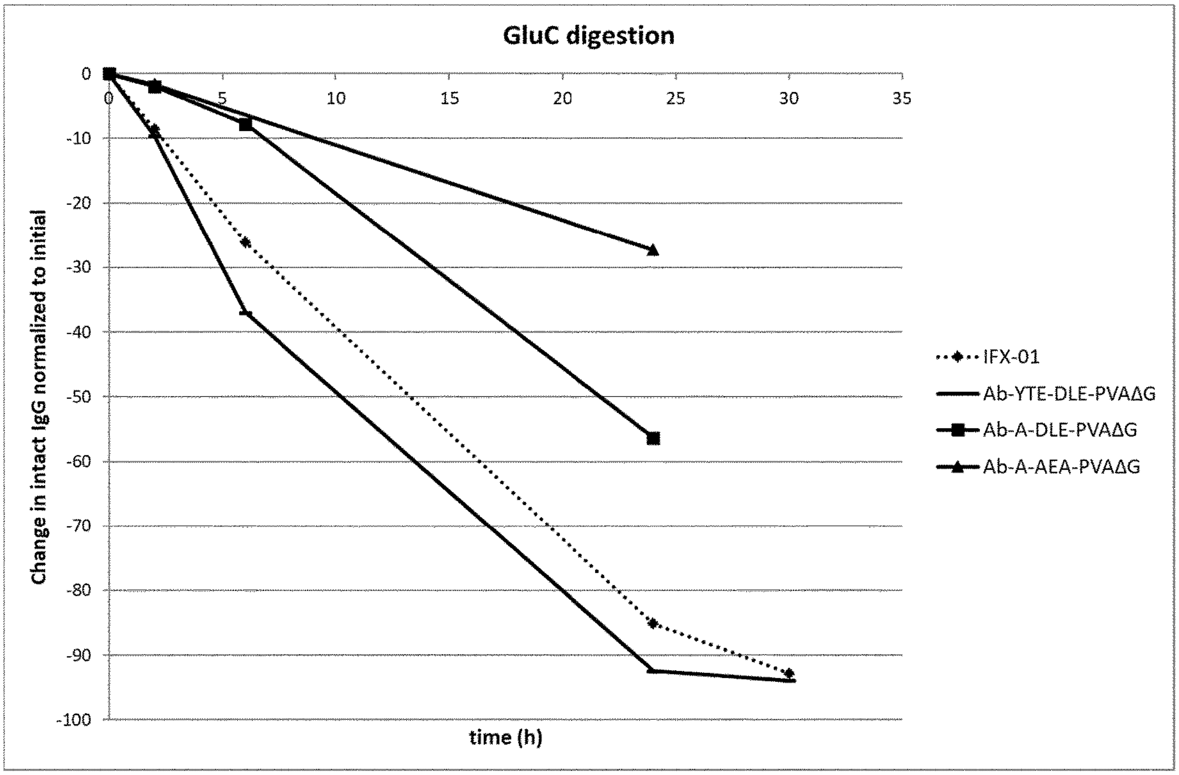
FIG. 9: Resistance to proteolytic degradation by GluC.

Results:

The tested antibody variants showed excellent resistance to proteolytic degradation by MMP-3 and IdeS, and good resistance to degradation by GluC (see FIGS. 7-9).

The invention claimed is:

1. An antibody comprising a TNFα-binding domain and an FcRn binding site, wherein said antibody comprises (i) a $V_L$ domain comprising a CDR1 region having the amino acid sequence as shown in SEQ ID NO:3, a CDR2 region having the amino acid sequence as shown in SEQ ID NO:4, and a CDR3 region having the amino acid sequence as shown in SEQ ID NO:5, and (ii) a $V_H$ domain comprising a CDR1 region having the amino acid sequence as shown in SEQ ID NO:6, a CDR2 region having the amino acid sequence as shown in SE ID NO:7, and a CDR3 region having the amino acid sequence as shown in SEQ II) NO:8, wherein the amino acid sequence of the antibody further comprises:

(i) the amino acids 233P, 234V, 235A, and a deletion at amino acid position 236;

(ii) the amino acid 434A or the amino acids 252Y, 254T and 256E; and (iii) the amino acids 239D, 330L, and 332E, wherein the numbering of amino acid residues is according to the EU index.

2. The antibody of claim 1, wherein the amino acid sequence of the antibody comprises the amino acids 233P, 234V, 235A, 239D, 330L, 332E and 434A, and a deletion at amino acid position 236.

3. The antibody of claim 1, wherein the amino acid sequence of the antibody comprises the amino acids 233P, 234V, 235A, 239D, 330L, 332E, 252Y, 254T and 256E, and a deletion at amino acid position 236.

4. The antibody of claim 1, having an affinity to human FcRn at pH 6 that is characterized by a dissociation constant $K_D$ of less than 300 nM, and having no affinity or low affinity to human FcRn at pH 7.4, characterized by a dissociation constant $K_D$ of greater than 10 μM.

5. The antibody of claim 1, which binds to human TNFα with a $K_D$ of less than 100 pM.

6. The antibody of claim 1, wherein said antibody is capable of being transported across a polarized cell monolayer from the apical side to the basolateral side in greater amount than a control antibody comprising a light chain having the amino acid sequence as shown in SEQ ID NO:1 and a heavy chain having the amino acid sequence as shown in SEQ ID NO:2.

7. The antibody of claim 1, which is more resistant to proteolytic degradation by MMP-3 and IdeS than infliximab.

8. A nucleic acid encoding the antibody of claim 1.

9. A method of treating an inflammatory condition comprising the step of administering an effective amount of the antibody of claim 1 to a subject in need thereof.

10. The method according to claim 9, wherein the inflammatory condition is an inflammatory disorder of the gastrointestinal tract.

11. The method according to claim 9, wherein said treatment comprises orally administering an effective amount of said antibody.

12. The method according to claim 9, wherein said antibody is applied topically.

13. A pharmaceutical composition comprising the antibody of claim 1.

* * * * *

UNITED STATES PATENT AND TRADEMARK OFFICE

CERTIFICATE OF CORRECTION

PATENT NO. : 11,472,872 B2
APPLICATION NO. : 16/648147
DATED : September 11, 2018
INVENTOR(S) : Esther Maria Furrer It is certified that error appears in the above-identified patent and that said Letters Patent is hereby corrected as shown below:

In the Specification

At Column 26, Line 24, replace the term "PVΔG" with the term -- PVAΔG --.

At Column 26, Line 27, replace the term "PVΔG" with the term -- PVAΔG --.

At Column 26, Line 64, replace the term "PVΔG" with the term -- PVAΔG --.

At Column 26, Line 67, replace the term "PVΔG" with the term -- PVAΔG --.

At Column 27, Line 39, replace the term "PVΔG" with the term -- PVAΔG --.

At Column 28, Line 9, replace the term "PVΔG" with the term -- PVAΔG --.

At Column 28, Line 11, replace the term "PVΔG" with the term -- PVAΔG --.

Signed and Sealed this
Twenty-first Day of March, 2023

Katherine Kelly Vidal

Katherine Kelly Vidal
*Director of the United States Patent and Trademark Office*